(12) United States Patent
Qin et al.

(10) Patent No.: US 10,493,170 B1
(45) Date of Patent: Dec. 3, 2019

(54) TARGETED GRAPHENE QUANTUM DOT-BASED THERANOSTICS

(71) Applicants: Yiru Qin, Tampa, FL (US); Shu-Feng Zhou, Tampa, FL (US)

(72) Inventors: Yiru Qin, Tampa, FL (US); Shu-Feng Zhou, Tampa, FL (US)

(73) Assignee: University of South Florida, Tampa, FL (US)

( * ) Notice: Subject to any disclaimer, the term of this patent is extended or adjusted under 35 U.S.C. 154(b) by 731 days.

(21) Appl. No.: 14/747,321

(22) Filed: Jun. 23, 2015

Related U.S. Application Data

(60) Provisional application No. 62/016,228, filed on Jun. 24, 2014.

(51) Int. Cl.
| | | |
|---|---|---|
| *A61K 49/00* | (2006.01) | |
| *A61K 31/704* | (2006.01) | |
| *A61K 47/02* | (2006.01) | |
| *A61K 47/22* | (2006.01) | |
| *A61B 5/00* | (2006.01) | |
| *A61N 5/06* | (2006.01) | |

(52) U.S. Cl.
CPC ......... *A61K 49/005* (2013.01); *A61B 5/0071* (2013.01); *A61K 31/704* (2013.01); *A61K 47/02* (2013.01); *A61K 47/22* (2013.01); *A61N 5/062* (2013.01)

(58) Field of Classification Search
None
See application file for complete search history.

(56) References Cited

U.S. PATENT DOCUMENTS 8,664,637 B2    3/2014    Jang et al.

FOREIGN PATENT DOCUMENTS

| CN | 103265020 A | 8/2013 |
|---|---|---|
| CN | 103432590 A | 12/2013 |

OTHER PUBLICATIONS

Xiong et al. Synthesis, characterization, and in vivo targeted imaging of amine-functionalized rare-earth up-converting nanophosphors. 2009 Biomaterials 30: 5592-5600.*
Yuan et al. New generation of chitosan-encapsulated ZnO quantum dots loaded with drug: synthesis, characterization and in vitro drug delivery response. 2010 Acta Biomaterialia 6: 2732-2739.*
Muhammad et al. Acid degradable ZnO quantum dots as a platform for targeted delivery of an anticancer drug. 2011 J. Mater. Chem. 21: 13406-13412. (Year: 2011).*
Shen et al. Facile preparation and upconversion luminescence of graphene quantum dots. 2011 Chem. Commun. 47: 2580-2582. (Year: 2011).*
Sun et al. Nano-graphene oxide for cellular imaging and drug delivery. 2008 Nano Res. 1: 203-212. (Year: 2008).*
Baalousha et al. Nanoparticle dispersity in toxicology. 2013 Nat. Nanotechnol. 8: 308-309. Published May 7, 2013. (Year: 2013).*
Shmeeda et al. Intracellular uptake and intracavitary targeting of folate-conjugated liposomes in a mouse lymphoma model with up-regulated folate receptors. 2006 Mol. Cancer Ther. 5: 818-824. (Year: 2006).*
Shen et al. Graphene quantum dots: emergent nanolights for bioimaging, sensors, catalysis and photovoltaic devices. 2012 Chem. Commun. 48: 3686-3699. (Year: 2012).*
Phosphate buffered saline (PBS) pH 7.4 product information page. Sigma-Aldrich website, sigmaaldrich.com/catalog/product/sigma/806552?lang=en&region=US. Accessed Aug. 6, 2018. (Year: 2018).*
Sun et al. Quantum-sized carbon dots for bright and colorful photoluminescence. 2006 J. Am. Chem. Soc. 128: 7756-7757. (Year: 2006).*
Mei-Ling Chen, et al. "Quantum-Dot-Conjugated Graphene as a Probe for Simultaneous Cancer-Targeted Fluorescent Imaging, Tracking, and Monitoring Drug Delivery", Bioconjugate Chemistry, 24, 387-397 (2013).
Abdullah-Al-Nahain, et al. "Target Delivery and Cell Imaging Using Hyaluronic Acid-Functionalized Graphene Quantum Dots", Mol. Pharmaceutics, 10, 3736-3744 (2013).
Israa Al-Ogaidi, et al. "Detection of the Ovarian Cancer Biomarker CA-125 Using Chemiluminescence Resonance Energy Transfer to Graphene Quantum Dots", Chem. Commun., 50, 1344-1346 (2014).
Preeti Nigam, et al. "Graphene Quantum Dots Conjugated Albumin Nanoparticles for Targeted Drug Delivery and Imaging of Pancreatic Cancer", J. Mater. Chem. B., 2, 3190-3195 (2014).
Minghan Xu et al., "Hydrothermal/Solvothermal Synthesis of Graphene Quantum Dots and Their Biological Applications", Nano Biomed Eng., 5.2:65-71 (2013).
Dengyu Pan et al., "Hydrothermal Route for Cutting Graphene Sheets into Blue-Luminescent Graphene Quantum Dots", Advanced Materials, 22.6:734-738 (2010).
Yonghun Shin et al., "Mass Production of Graphene Quantum Dots by One-Pot Synthesis Directly from Graphite in High Yield", Small, 10.5:866-870 (2014).

* cited by examiner

*Primary Examiner* — Jennifer A. Lamberski
(74) *Attorney, Agent, or Firm* — Thomas|Horstemeyer, LLP

(57) ABSTRACT

Conjugates are provided containing a graphene quantum dot, a targeting moiety, and an active agent. The conjugates can be used to provide one or more therapeutic, prophylactic, or diagnostic effects to a subject in need thereof. The subject can be a cancer patient and the active agent an anti-cancer agent. The graphene quantum dots can have an average particle size of about 1-20 nm and a monodisperse size distribution. The size distribution can have a span about 1 or less and/or a coefficient of variance of about 0.5 or less. Methods of making the conjugates are provided. The methods can include conjugating the targeting moiety to the GQD using a reactive coupling group. Methods of treating, preventing, and/or diagnosing a disease or disorder in a patient in need thereof by administering the conjugates are provided.

6 Claims, 26 Drawing Sheets

TARGETED GRAPHENE QUANTUM DOT-BASED THERANOSTICS

CROSS-REFERENCE TO RELATED APPLICATIONS

This application claims priority to U.S. Ser. No. 62/016,228 filed Jun. 24, 2014.

BACKGROUND

Cancer remains one of the most devastating diseases worldwide. According to the cancer report by American Cancer society, cancer remains the second leading cause of death in US accounting for approximately 5.8 million of deaths in 2013 (Siegel, Naishadham et al. 2013). Current management of cancer, including surgery, chemotherapy and radiation, faces multiple challenges. These challenges include severe adverse side effect and poor effectiveness, especially when metastasis occurs. Early diagnosis and targeted therapy are well known to improve survival rate and the quality of life for cancer patients. The major challenges of cancer are being diagnosed at late stages resulting metastatic and limited selectivity of chemotherapy. A major challenge of cancer therapy is preferential destruction of malignant cells with sparing of normal tissue.

Multiple, complementary techniques for tumor detection, including magnetic resonance, scintigraphic and optical-imaging, are under active development. Each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules. Conventional quantum dots (QD) have been of great potential in bioimaging and diagnosis applications. However, the safety issue limited their usage in clinical. Graphene and graphene quantum dots have seen attention as useful materials in a range of applications, including optics, electronics, and biomedical applications. Among them, biomedical applications of GQDs represent a relatively new but fast growing area, for example, bioimaging, biosensor materials, and drug delivery.

Targeted imaging of cancer remains an important but elusive goal. Such imaging could provide early diagnosis, detection of metastasis, aid treatment planning and benefit therapeutic monitoring. By leveraging the expanding list of specific molecular characteristics of tumors and their microenvironment, molecular imaging also has the potential to generate tumor-specific reagents. But many efforts at tumor-specific imaging are fraught by nonspecific localization of the putative targeted agents, eliciting unacceptably high background noise.

Cancer therapies have also advanced considerably during the last few decades. However, they are also still hampered by nonspecific delivery of anti-tumor agents to normal cells, resulting in horrendous side effects for patients. This lack of specificity also results in lower efficacy of treatments due to the want of a capability to deliver active agents in a focused manner where they are most needed, i.e. to cancer cells alone.

It is therefore an object of this disclosure to provide materials, compositions, and methods for combined therapy and diagnosis (theranostics) of various cancers and related disorders.

It is also an object of this disclosure to provide materials compositions, and methods to improve specificity and/or efficacy for treatment of various cancers and related disorders.

An additional object of the disclosure is to provide materials compositions, and methods to simultaneously deliver an active agent to and monitor the treatment of various cancers and related disorders.

SUMMARY

Conjugates are provided containing a graphene quantum dot (GQD), a targeting moiety conjugated to the GQD, and an active agent associated covalently or non-covalently with the GQD. The GQDs can have a monodisperse size distribution. The GQDs can have an average diameter of between 1.0 and 20.0 nm, between 2.0 and 10.0 nm, or between 2.0 and 5.0 nm. The monodisperse size distribution can have a span of about 1 or less. The monodisperse size distribution can have a coefficient of variation of about 0.5 or less. In some embodiments, about 40% or more, preferably about 50% or more, of the GQDs have a diameter within ±0.5 nm of the average diameter of the GQDs.

The targeting moiety can target the conjugate to a specific cell, tissue, organ, or local in a subject or patient. The targeting moiety can be a protein, a peptide, a nucleic acid, or a small molecule. The targeting moiety can be folic acid or a derivative thereof.

The active agent can be a therapeutic, prophylactic, or diagnostic agent. The agent can be a small molecule. The active agent can be an anti-cancer agent. The active agent can be doxorubicin. The active agent can be non-covalently associated with the GQD via π-bonding, cation-π, Van der Walls, or hydrogen-bonding interactions. The active agent can have aromatic groups that non-covalently associate with the GQD via π-bonding interactions.

Pharmaceutical formulations containing the conjugates and a pharmaceutically acceptable carrier are provided. The pharmaceutical formulations can include excipients such as sugars or sugar alcohols, buffering agents, preservatives, carriers, antioxidants, chelating agents, water-soluble natural or synthetic polymers, cryoprotectants, lyoprotectants, surfactants, bulking agents, or stabilizing agents.

Methods of making the conjugates are provided. The methods include conjugating a targeting moiety to a GQD to form a first intermediate; and associating an active agent to the first intermediate to form the conjugate. The method can include making GQDs by a method of combining a graphene source with a strong oxidizing mixture to form a combination; and heating the combination to an elevated temperature with respect to room temperature to produce the GQDs. The graphene source can be carbon black, graphite, or a combination thereof. The elevated temperature can be about 100° C. or more, for example about 100° C. to 200° C. or about 120° C. to 180° C. In some embodiments the heating is for a period of time of about 2 hours or less.

The oxidizing mixture can include oxidizing agents such as permanganates, hexafluoromanganates, persulfates, chromates, Fenton's reagent, oxidizing acids, and combinations thereof. The permanganates can include sodium permanganate, potassium permanganate, or calcium permanganate. The persulfates can include sodium peroxomonosulfate, sodium persulfate, potassium peroxymonosulfate, or ammonium persulfate. Oxidizing acids can include nitric acid, perchloric acid, chloric acid, chromic acid, sulfuric acid, and combinations thereof. In some embodiments the oxidizing mixture contains three or more oxidizing agents. In some embodiments the oxidizing mixture contains at least two oxidizing acids. In preferred embodiments the oxidizing mixture contains potassium permanganate, nitric acid, and sulfuric acid.

Methods of treating and diagnosing a disease or disorder including administering the conjugates to a patient in need thereof are provided. The patient can have cancer. In some embodiments the method includes fluorescence imaging of the conjugates in the patient. The methods can include irradiating the conjugates with near-IR light to release the active agent at the intended site within the patient.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
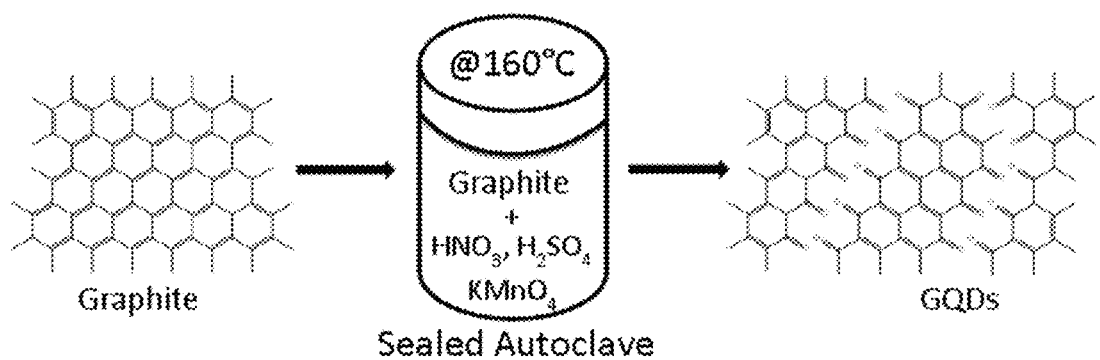
FIG. 1 is a schematic of one embodiment of a method of making graphene quantum dots. Graphite is combined with an oxidizing mixture of $HNO_3$, $H_2SO_4$, and $KMnO_4$ in a sealed autoclave and heated to 160° C. to produce graphene quantum dots having a monodisperse size distribution.

Conjugates are provided containing a graphene quantum dot (GQD), a targeting moiety conjugated to the GQD, and an active agent associated covalently or non-covalently with the GQD. Pharmaceutical formulations containing the conjugates are provided, for example for therapeutic, diagnostic, or theranostic applications. Methods of making the conjugates and formulations thereof are also provided, as are methods of using the conjugates and formulations thereof for the treatment and/or diagnosis of a disease or disorder.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

As used herein, the term "graphene quantum dot" or "GQD" refers to a nanocrystalline graphene material in which excitons are confined in all three spatial dimensions, as distinguished from quantum wires (quantum confinement in only two dimensions), quantum wells (quantum confinement in only one dimension), and bulk semiconductors (unconfined). Graphene quantum dots can contain from about 1 to 10, about 1 to 5, about 1 to 4, or about 1 to 3 layers of small pieces of graphene sheets, the edges of which may contain chemical defects such as from oxidation of the graphene. Also, many optical, electrical and chemical properties of the graphene quantum dot may be strongly dependent on its size, and hence such properties may be modified or tuned by controlling its size. A graphene quantum dot may generally be characterized as a particle, the shape of which may be spheroidal, ellipsoidal, or other shape. The "size" of the graphene quantum dot may refer to a dimension characteristic of its shape or an approximation of its shape, and thus may be a diameter, a major axis, a predominant length, etc. The size of a graphene quantum dot is on the order of nanometers, i.e., generally about 1 nm to 1000 nm, but more typically about 1 nm to 100 nm, about 1 nm to 30 nm, about 1 nm to 20 nm, about 1 nm to 10 nm, or about 1 nm to 5 nm. In a plurality or ensemble of graphene quantum dots, the graphene quantum dots may be characterized as having an average size. The size distribution of a plurality of graphene quantum dots may or may not be monodisperse. Graphene quantum dots are described, for example, in Sun et al., *Materials Today,* 2013, 16(11):433-442.

The term "graphene", as used herein, refers to two dimensional sheet of hexagonal carbon that includes single-layer graphene and few-layer graphene. The term "few-layer" graphene includes graphene having about 2-10 layers, preferably about 3-7 layers. The term "exfoliated graphite" includes about 11 layers of hexagonal carbon, or more. For example, exfoliated graphite can include about 11 layers of more of graphene that has been intercalated and subsequently removed from bulk graphite. The term "exfoliate," as used herein, refers to an expansion of a bulk graphite lattice. The term "graphite" is meant to include intercalated graphite, exfoliated graphite, and in some aspects, graphene.

The term "carbon black", as used herein, refers to the materials commonly referred to as carbon black and includes cetylene black, channel black, furnace black, lamp black and thermal black. Carbon black can be produced, for example, by the incomplete combustion of heavy petroleum products.

The term "particle size" and "particle diameter", as used interchangeably herein, mean the average diameter of the image of the particle as viewed by electron microscopy, unless otherwise stated. The size distribution of a collection of particles can be characterized by several values. The term "average particle size" and "average particle diameter" mean the number average of the particle sizes of a collection of particles.

The "span" for a distribution of particles can be computed from the formula $$\mathrm{Span} = \frac{D_{v0.9} - D_{v0.1}}{D_{v0.5}};$$

where $D_{v0.1}$, $D_{v0.5}$, and $D_{v0.9}$ are defined such that 10%, 50%, and 90% of the particles in the collection of particles have a dimension smaller than $D_{v0.1}$, $D_{v0.5}$, and $D_{v0.9}$ respectively.

The coefficient of variation (COV) for a collection of particles is the standard deviation of particle sizes divided (normalized) by the average particle size.

The term "monodisperse", as used herein, characterizes a collection of particles where the particle size scatter is within a narrow range of sizes. A monodisperse collection of particles can be a collection of particles having a span of about 2 or less, about 1 or less, about 0.8 or less, or about 0.5 or less. A monodisperse collection of particles can be a collection of particles having a COV of about 0.5 or less, about 0.4 or less, or about 0.3 or less. A monodisperse collection of particles can be a collection of particles wherein about 40% or more, about 50% or more, about 60% or more, about 70% or more, or about 80% or more of the particles have a particle size that is within ±10 nm, ±8 nm, ±6 nm, ±5 nm, or ±3 nm of the average particle size for the collection of particles.

The terms "standard electrode potential" and "standard potential", as used interchangeably herein, refer to the potential (voltage) developed by a reversible electrode when the activities of all ions in the cell are unity, all gases are at 1 atm pressure, and all solids are in their most stable form at 25° C. The "standard electrode potential" can be reported as a reduction potential. The "standard electrode potential" of a species, $M^{n+}$, can be measured against the standard hydrogen electrode as the potential of the right-hand electrode less that of the left-hand electrode in the cell:

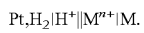

$Pt,H_2|H^+||M^{n+}|M.$

The "standard electrode potential" can be used as one measure of the oxidizing ability or strength of an oxidizing agent. Unless otherwise indicated, standard electrode potentials reported herein are reduction potentials and the larger (more positive) the standard electrode potential the stronger the oxidizing ability of the oxidizing agent.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "subject" refers to any individual who is the target of administration. The subject can be a vertebrate, for example, a mammal. Thus, the subject can be a human. The term does not denote a particular age or sex. The term "patient" refers to a subject afflicted with a disease or disorder. The term "patient" includes human and veterinary subjects.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal which may be predisposed to the disease, disorder and/or condition but has not yet been diagnosed as having it.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

"Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

transdermal

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

Conjugates and Formulations Thereof

Conjugates are provided containing a graphene quantum dot (GQD), a targeting moiety, and a therapeutic, prophylactic, and/or diagnostic agent. Conjugates can contain additional moieties and can be administered individually or in combination with one or more additional active agents. The conjugates can have a combination of one or more therapeutic, prophylactic, or diagnostic effects. For example, the conjugates can target a specific tissue, organ, or local associated with a specific disease; can be used to image the tissue, organ, or local; can release a therapeutic or prophylactic agent at the tissue, organ, or local; or a combination thereof.

Graphene Quantum Dots (GQDs)

The conjugate contains a graphene quantum dot (GQD). The graphene quantum dot can contain 1 to 10, 1 to 5, 1 to 4, or 1 to 3 layers of small pieces of graphene sheets. The size of a graphene quantum dot is generally about 1-1,000 nm, but more typically about 1-100 nm, about 1-20 nm, about 1-10 nm, or about 2-5 nm. A plurality of the graphene quantum dots may or may not have a monodisperse size distribution, although monodisperse size distributions are preferred.

The GQDs can have an average diameter of about 1.0-20.0 nm, about 2.0-10.0 nm, or about 2.0-5.0 nm. The monodisperse size distribution can have a span of less than 1.5, less than 1.0, less than 0.8, or less than 0.6. The monodisperse size distribution can have a coefficient of variation of less than about 0.5. In some embodiments, at least 40%, preferably at least 50%, of the GQDs in a plurality of GQDs have a diameter within ±0.5 nm of the average diameter of the GQDs.

The edges and/or surfaces of the graphene quantum dot may contain chemical defects such as from oxidation of the graphene. The defects can include gaps or boundaries between crystals of graphene. Other examples of defects include covalent defects or Stone-Wales type defects where carbon atoms are bonded in rings of different numbers of atoms such as 5 atoms or 7 atoms, instead of 6 atoms. Defects can include topological distortions that may form defects. The defects can include chemical defects such as epoxides, ketones, alcohols, and/or carboxylic acids. The defects can be used to associate and/or bond one or more moieties or groups to the GQD. For example, the defects can be reacted to associate with or conjugate to targeting moieties. In some embodiments the defects can be converted into a reactive coupling group.

The GQD can have a fluorescence emission that can be used, for example, to image conjugate in vivo. The GQD can have a fluorescence emission that is from 450-600 nm, 450-550 nm, or 475-525 nm.

Targeting Moieties

The conjugates include one or more targeting moieties conjugated to the GQD. The targeting moiety can be conjugated directly to the GQD, or can be conjugated to the GQD via a linker or a polymer that is attached to the GQD.

The targeting moiety can be a peptide. The targeting moiety can be a protein such as an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The targeting moiety of the conjugate can be an antibody or antigen binding fragment thereof. The targeting elements moieties should have an affinity for a cell-surface receptor or cell-surface antigen on the target cells. The targeting moiety can be a nucleic acid targeting moiety. The targeting moiety can be a small molecule. The targeting moieties may result in internalization of the particle within the target cell.

The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

The targeting moiety may specifically bind to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melonoma associated antigens, etc.).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.*, 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature*, 366:473 (1993); GenBank Acc. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/MART-1 (Kawakami, et al., *Proc. Nat. Acad. Sci. USA*, 91:3515 (1994); GenBank Acc. Nos. U06654 and U06452), tyrosinase (Topalian, et al., *Proc. Nat. Acad. Sci. USA*, 91:9461 (1994); GenBank Acc. No. M26729; Weber, et al., *J. Clin. Invest*, 102:1258 (1998)), Gp-100 (Kawakami, et al., *Proc. Nat. Acad. Sci. USA*, 91:3515 (1994); GenBank Acc. No. S73003, Adema, et al., *J. Biol. Chem.*, 269:20126 (1994)), MAGE (van den Bruggen, et al., *Science*, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, J. Exp. Med., 121:439 (1985); GenBank Acc. Nos. M59710, M59255 and M29540), and PyLT (GenBank Acc. Nos. J02289 and J02038); p97 (melano-transferrin) (Brown, et al., *J. Immunol.*, 127:539-46 (1981); Rose, et al., *Proc. Natl. Acad. Sci. USA*, 83:1261-61 (1986)). Additional tumor associated antigens include prostate surface antigen (PSA) (U.S. Pat. Nos. 6,677,157; 6,673,545); β-human chorionic gonadotropin β-HCG) (McManus, et al., *Cancer Res.*, 36:3476-81 (1976); Yoshimura, et al., *Cancer*, 73:2745-52 (1994); Yamaguchi, et al., Br. *J. Cancer*, 60:382-84 (1989): Alfthan, et al., *Cancer Res.*, 52:4628-33 (1992)); glycosyltransferase β-1,4-N-acetylgalactosaminyltransferases (GalNAc) (Hoon, et al., *Int. J. Cancer*, 43:857-62 (1989); Ando, et al., *Int. J. Cancer*, 40:12-17 (1987); Tsuchida, et al., J. Natl. *Cancer*, 78:45-54 (1987); Tsuchida, et al., *J. Natl. Cancer*, 78:55-60 (1987)); NUC18 (Lehmann, et al., *Proc. Natl. Acad. Sci. USA*, 86:9891-95 (1989); Lehmann, et al., *Cancer Res.*, 47:841-45 (1987)); melanoma antigen gp75 (Vijayasardahi, et al., *J. Exp. Med.*, 171:1375-80 (1990); GenBank Accession No. X51455); human cytokeratin 8; high molecular weight melanoma antigen (Natali, et al., *Cancer*, 59:55-63 (1987); keratin 19 (Datta, et al., *J. Clin. Oncol.*, 12:475-82 (1994)).

Targeting moieties can include derivatives of known targeting moieties, for example derivatives having reactive coupling groups that can be used to bond the targeting moiety to the GQD or to a polymer or other molecule. In some embodiments the targeting moiety targets the folate receptor, for example the targeting moiety can be folic acid or a folic acid derivative.

Active Agent

The conjugates contain one or more active agents, e.g. one or more therapeutic, prophylactic, or diagnostic agents. The active agent can be associated covalently or non-covalently with the conjugate. The association is preferably labile such that the conjugate can release the active agent at the appropriate time and location to be effective. For example, the association can be such that a therapeutically effective amount of a therapeutic agent is released at the site to achieve one or more beneficial therapeutic effects.

The active agent can be a therapeutic agent. Exemplary therapeutic agents include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof. In some embodiments, the therapeutic agent is a small molecule and/or organic compound with pharmaceutical activity.

In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or nonsteroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, antispasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis, etc. Exemplary therapeutic agents that can be incorporated into the particles include, but are not limited to. tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Prophylactic agents that can be included in the conjugates include, but are not limited to, antibiotics, nutritional supplements, and vaccines. Vaccines may be isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents can include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens. Neisseria meningitidis, Neisseria gonorrhoeae, Streptococcus mutans, Pseudomonas aeruginosa, Salmonella typhi, Haemophilus* parainfluenzae. *Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis. Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Additional Moieties

The conjugate can contain one or more additional moieties. For example, the conjugate can contain one or more polymers.

The conjugate can include one or more polymers. The polymers can coat and protect the conjugate. The polymer can be a biodegradable polymer. The biodegradable polymer can be an enteric polymer that protects the conjugate from the acidic environments in the gut. The polymer can be a stealth polymer.

Stealth polymers, as used herein, refer to polymers that help prevent or reduce recognition of the conjugates by RES and/or Kupffer cells, for example by modification of the surface properties of conjugates to prevent opsonin interactions and subsequent phagocyte clearance. Stealth polymers can include natural, semi-synthetic, or synthetic polymers. Stealth polymers can include polysaccharides such as dextran, polysialic acid, hyaluronic acid, chitosan, heparin, and copolymers thereof. Stealth polymers can include polyvinyl pyrrolidone (PVP), polyvinyl alcohol (PVA), polyacrylamide (Pam), and copolymers thereof. Stealth polymers can include poly(alkylene glycols) and poly(alkylene oxides) such as poly(ethylene glycol), poly(propylene glycol), poly (ethylene oxide), or poly(propylene oxide). Stealth polymers can include copolymers of two or more stealth polymers.

Biodegradable polymers can include polymers that are insoluble or sparingly soluble in water that are converted chemically or enzymatically in the body into water-soluble materials. Biodegradable polymers can include soluble polymers crosslinked by hydolyzable cross-linking groups to render the crosslinked polymer insoluble or sparingly soluble in water. Biodegradable polymers in the conjugate can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof.

Pharmaceutical Formulations

Pharmaceutical formulations are provided that contain an effective amount of conjugates in a pharmaceutical carrier appropriate for administration to an individual in need thereof. The formulations can be administered parenterally (e.g., by injection or infusion), topically (e.g., to the eye), or via pulmonary administration.

Parenteral Formulations

The conjugates can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the conjugates can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or conjugates.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the conjugates in the required amount in the appropriate solvent or dispersion medium with one or more of the excipients listed above, as required, followed by filtered sterilization. Generally, dispersions are prepared by incorporating the various sterilized conjugates into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the conjugates plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

Topical Formulations

The conjugates can be formulated for topical administration. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the conjugates can be administered as a liquid formulation, such as a solution or suspension, a semi-solid formulation, such as a lotion or ointment, or a solid formulation. In some embodiments, the conjugates are formulated as liquids, including solutions and suspensions, such as eye drops or as a semi-solid formulation, such as ointment or lotion for topical application to the skin, to the mucosa, such as the eye or vaginally or rectally.

The formulation may contain one or more excipients, such as emollients, surfactants, emulsifiers, penetration enhancers, and the like.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase can contain a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of the conjugates in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams can include an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more conjugates to a patient in need thereof. For topical applications, repeated application can be done or a patch can be used to provide continuous administration of the noscapine analogs over an extended period of time.

Enteral Formulations

The conjugates can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The conjugates may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers and/or pH dependent polymers, with or without water insoluble/water soluble non polymeric excipient, to produce the desired release profile. The coating is either performed on dosage form (matrix or simple) which includes, but not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

Methods of Making Conjugates and Formulations Thereof

Methods of Making GQDs

The GQD can be made by any method known to the skilled artisan. Preferred methods include those that produce a monodisperse particle size distribution. In some embodiments a method that does not produce GQDs with a monodisperse size distribution can be used. In some embodiments the GQDs are size-filtered to provide a more monodisperse size distribution.

The methods include combining a graphene source with a strong oxidizing mixture to form a combination; and heating the combination to an elevated temperature to produce the GQDs. The methods can be performed in a single-step, e.g. the methods can be performed without the need to produce graphene oxide. The graphene source can be carbon black, graphite, or a combination thereof. The elevated temperature can be can be about 100° C. or more, for example about 100° C. to 200° C., about 120° C. to 180° C., or about 140° C. to 160° C. In some embodiments the heating is for a period of time of about 5 hours, 4 hours, 3 hours, 2.5 hours, 2.0 hours, 1.5 hours, 1.0 hours, or less. In some embodiments the heating is for a period of time less than 2 hours, less than 1.5 hours, or less than 1 hour.

Strong Oxidizing Mixture

The methods can include combining the graphene source with a strong oxidizing mixture. The strong oxidizing mixture can include oxidizing agents such as permanganates, hexafluoromanganates, persulfates, chromates, Fenton's reagent, oxidizing acids, and combinations thereof. The strong oxidizing mixture can have a standard electrode potential or can contain at least one, two, three, or more oxidizing agents having a standard electrode potential wherein the standard electrode potential is about 0.5 V to 5 V, about 0.9 V to 3.0 V, about 1.0 V to 2.5 V, about 1.0 V to 2.0 V, about 1.0 V to 1.6 V, or about 1.2 V to 1.6 V. In some embodiments at least one, two, three, or more oxidizing agents have a standard electrode potential that is about 0.9 V, 1.0V, 1.1 V, 1.2 V, 1.3 V, 1.4 V, or greater and a standard electrode potential that is about 5.0 V, 4.0 V, 3.5 V, 3.0 V, 2.5 V, 2.0 V, or less.

The strong oxidizing mixture can include at least one, two, three, or more oxidizing agents selected from of permanganates, hexafluoromanganates, persulfates, and chromates. The strong oxidizing mixture can include at least one, two, three, or more strong oxidizing agents selected from a permanganate, a peroxydisulfate, a bromate, a perchlorate, a chlorate, manganese dioxide, nitrous oxide, and ozone. The permanganate can be, for example, potassium permanganate, ammonium permanganate, calcium permanganate, sodium permanganate, or silver permanganate.

The oxidizing mixture can include oxidizing agents such as permanganates, hexafluoromanganates, persulfates, chromates, Fenton's reagent, oxidizing acids, and combinations thereof. The permanganate can include sodium permanganate, potassium permanganate, or calcium permanganate. The persulfate can include sodium peroxomonosulfate, sodium persulfate, potassium peroxymonosulfate, or ammonium persulfate. Oxidizing acid can include nitric acid, perchloric acid, chloric acid, chromic acid, sulfuric acid, and combinations thereof. In some embodiments the oxidizing mixture contains three or more oxidizing agents. In some embodiments the oxidizing mixture contains at least two oxidizing acids. The oxidizing acids can include nitric acid, perchloric acid, chloric acid, chromic acid, and sulfuric acid.

In some embodiments the oxidizing mixture can contain a permanganate such as potassium permanganate, nitric acid, and sulfuric acid.

Graphene Quantum Dots

The methods can be used to make small GQDs with a monodisperse size distribution. Graphene quantum dots (GQDs) are provided. The GQDs can be prepared by one of the methods described herein. The methods provide a plurality of GQDs having a small size and/or a monodisperse size distribution. Compositions are provided containing the plurality of GQDs. The GQDs can have an average diameter of about 1.0 nm to 20.0 nm, about 2.0 nm to 10.0 nm, or about 2.0-5.0 nm. The monodisperse size distribution can have a span of less than 1, e.g. about 1.0, 0.9, 0.8, 0.7 or less. The monodisperse size distribution can have a coefficient of variation of less than about 0.5, e.g. about 0.5, 0.4 0.3, 0.25 or less. In some embodiments, at least 40%, at least 50%, at least 60%, or at least 75% of the GQDs have a diameter within ±0.5 nm of the average diameter of the GQDs. The GQDs can have a lattice spacing of about 0.25 nm, 0.24 nm, 0.23 nm, 0.22 nm, or less.

Methods of Conjugating Targeting Moieties

The targeting moieties can be conjugated to the GQD using many methods known to the skilled artisan. In some embodiments the targeting moieties are conjugated to defects on the GQD. In some embodiments the targeting moieties include aldehyde reactive linking groups such as hydrazides, alkoxyamines, and primary amines that can react with defects in the GQD to form covalent bonds.

In some embodiments the graphene quantum dots are reacted to introduce reactive coupling groups at the defects. For example, primary amines (—$NH_2$), aldehydes (—COH), or thiol groups (—SH) can be introduced into the defect sites of the GQD. Targeting moieties with amine-reactive linking groups, aldehyde-reactive linking groups, or sulfhydryl-reactive linking groups can be conjugated to the reactive coupling groups on the GQD to form covalent bonds. The coupling reaction may include the use of a catalyst, heat, pH buffers, light, or a combination thereof. In an exemplary embodiment, the GQD is reacted with ammonium hydroxide and hydrogen peroxide to introduce amine reactive coupling groups at the GQD defect sites. The targeting ligand is conjugated to the —$NH_2$ on the edge of GQDs by coupling with crosslinking agents.

Methods of Associating Agents

The agents such as therapeutic, prophylactic, or diagnostic agents can be associated with the GQD-targeting moiety conjugate either covalently or non-covalently. Covalent conjugation can be achieved as outlined above for the targeting moieties, preferably using a labile linker that can be degraded by changes in temperature, pH, or by enzymatic degradations.

In some embodiments the active agent is non-covalently associated with the GQD-targeting moiety conjugate. For example, the active agent can include cationic groups that associate with the GQD via cation-pi interactions. The active agent can include one or more aromatic groups that associate with the GQD via pi-stacking interactions. The association can be accomplished by mixing the active agent and the GQD-targeting moiety conjugate in the appropriate amounts.

Methods of Using Conjugates and Formulations Thereof

The conjugates and formulations thereof can be administered to a subject or patient in need thereof. In particular, the conjugates and formulations thereof can be administered to a patient in need of a therapeutic and diagnostic effect. In preferred embodiments the patient has cancer and the therapeutic effect is alleviating one or more symptoms associated with the disease, increasing the overall life expectancy of the patient, decreasing the tumor size, or a combination thereof.

In some embodiments the conjugate or a formulation thereof is administered to a patient and imaged to detect the presence and/or location of tumors. For example, the conjugates can localize to tumor tissue and fluorescence imaging of the conjugates can demonstrate the presence and/or size of tumors in the patient.

The conjugates can release the active agent at the target site. For example, the conjugates can release an anti-cancer agent at the site of the tumor. In some embodiments the conjugate is irradiated with light, for example, near-IR light to trigger release of the active agent at the tumor site. In some embodiments, in addition to releasing the active agent, the near-IR irradiation heats the GQD.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Materials

Graphite, potassium permanganate ($KMnO_4$), sodium carbonate ($Na_2CO_3$), hydrogen peroxide ($H_2O_2$), sulfuric acid ($H_2SO_4$), and nitric acid ($HNO_3$), phorbol myristate acetate (PMA), ribonuclease, propidium iodide (PI), dimethyl sulfoxide (DMSO) thiazolyl blue tetrazolium bromide (MTT), 1-(3-Dimethylaminopropyl)-3-ethylcarbodiimide hydrochloride (EDC), N-hydroxysuccinimide (NHS), folic acid (FA), and Doxorubicin (Dox) were purchased from Sigma-Aldrich Inc. (St. Louis, Mo., USA). 5-(and 6)-chloromethyl-2',7'-dichlorodihy-drofluorescein diacetate (CM-$H_2DCFDA$), RPMI 1640 medium, fetal bovine serum (FBS), penicillin and streptomycin, and phosphate buffered saline (PBS) were obtained from Invitrogen Inc. (Carlsbad, Calif., USA). Rapamycin (RAP), an autophagy inducer, and Hoechst 33342, a nucleus staining dye, were purchased from Enzo life sciences (Farmingdale, N.Y., USA). The polyvinylidene difluoride (PVDF) membrane was purchased from Millipore Inc. (Bedford, Mass., USA). Primary monoclonal antibodies against human E-cadherin, N-cadherin, vimentin, β-catenin, slug, and snail were purchased from Cell Signaling Technology Inc. (Beverly, Mass., USA). The antibodiy against human β-actin was purchased from Santa Cruz Biotechnology Inc. (Santa Cruz, Calif., USA). Visualization was performed using BioRad system (Hercules, Calif., USA) with electro-chemiluminescence substrate purchased from Pierce (Hudson, N.H., USA).

Measurement of Quantum Yield of GQDs

Quinine sulfate in 0.1 M $H_2SO_4$ (QY=0.543) was chosen as standard. The quantum yields of GQDs (in water) were calculated according to:

$$\phi_x = \phi_{st}\left(\frac{I_x}{I_{st}}\right)\left(\frac{\eta_x^2}{\eta_{st}^2}\right)\left(\frac{A_{st}}{A_x}\right)$$

Where $\Phi$ is the quantum yield, I is the measured integrated emission intensity, $\eta$ is the refractive index of the solvent, and A is the absorbance. The subscript "st" refers to standard with known quantum yield and "x" for the sample.

TABLE 1

Quantum yield of GQDs using quinine sulfate as a reference

| Sample | Integrated emission intensity (I) | Absorbance (A) | Refractive index of the solvent (η) | Quantum yield (φ) |
|---|---|---|---|---|
| Quinine sulfate | 3432500 | 0.0668 | 1.33 | 0.543 |
| GQDs | 1207000 | 0.0971 | 1.33 | 0.131 |

Characterization of GQDs-FA-Dox

The morphology characterization of GQDs was carried out using transmission electron microscopy (TEM, JEM 100CX), high-resolution transmission electron microscopy (HRTEM, Tecnai F20), and Fourier Transform Infrared Spectroscopy (FTIR, PerkinElmer spectrum 100 series).

Cell Culture

The normal ovarian epithelia cell line T80 and two ovarian carcinoma cell lines, OVCAR3 and SKOV3, were obtained from American Type Culture Collection (ATCC) (Manassas, Va., USA) was cultured in RPMI1640 medium containing 10% non-heated-inactivated FBS and 0.5% penicillin and streptomycin in a humidified incubator of 5% $CO_2$/95% air at 37° C. Cells were suspended in the culture medium.

Cell Viability Assay

Cells were treated with various concentrations of GQDs-FA-Dox (0, 0.25, 0.5, 1, 2, and 4 μM equivalent to Dox) for 24 h and 48 h, respectively. Cell viability was determined by the MTT assay. In brief, the cells were treated with GQDs-FA-Dox conjugates, 10 μL MTT (5 mg/ml) was added into each well and incubated for 4 h, culture medium was removed and 100 μL DMSO was added to dissolve formazan crystals. Absorbance was read at 560 nm for formazan and 670 nm for background by Synergy H4 hybrid multi-mode microplate reader (BioTek). The results were given as relative value to the control in percent.

Quantification of Apoptosis

Apoptotic cells were detected by FITC Annexin V apoptosis kit (eBiosciences, San Diego, Calif., USA) according to the manufacturer's instruction. In brief, macrophages were incubated with different concentrations of GQDs and different time points. Cells were washed with PBS, centrifuged and re-suspended in 100 μL binding buffer containing 5 μL of Annexin V-FITC and 5 μL of PI. After 15 min incubation at 37° C. in the dark, cells were analyzed using flow cytometer. Autophagy was quantified by measuring the dye-stained autolysosome in the cells using Cyto-ID autophagy detection kit (Enzo life sciences, Farmingdale, N.Y., USA). After treatment with GQDs for different times, the THP-1 derived macrophages were washed with PBS and re-suspended in 100 μL assay buffer containing 5 μL green detection reagent. After incubation for 10 min at 37° C., cells were washed with assay buffer and analyzed using flow cytometry.

Determination of Cellular Localization and Uptake

For the localization assay by confocal laser microscopy, the cells were seeded onto eight-chamber slides. The cells were cultured for 24 h, washed thrice with PBS, and then incubated with GQD-FA-Dox (1 μM) for 1 h. After washing thrice with cold PBS, cells were incubated by Hoechst 33342 for nuclear staining. After 10 min, the cells were washed again with PBS buffer. And fluorescence of cells was observed by confocal microscope (Olympus, Japan). Hoechst 33342 was excited with 405 nm laser, and signals were collected from 425 nm to 475 nm. GQDs and DOX were excited with 488 nm laser, and their signals were collected from 500 nm to 530 nm and 552 nm to 617 nm, respectively.

For the quantification of drug uptake assay by flow cytometry, the cells were seeded onto six-well plates. The cells were cultured for 24 h, washed thrice with PBS, and then incubated with GQD-FA-Dox and GQD-Dox (1 μM) for 1 h. And cells was then detached by 5% trypsin and washed with cold PBS. Cells were incubated with Hoechst 33342 for nuclear staining. After 10 min, the cells were washed again with PBS buffer and observed by flow cytometry (Olympus, Japan.

Western Blotting Assay

Cells were harvested and lysed with RIPA lysis buffer (Pierce, Rockford, Ill., USA) with protease inhibitor cocktail and centrifuged at 3,000 g for 10 min at 4° C. Proteins were resolved by 4×SDS-PAGE samples loading buffer (Bioworld, Atlanta, Ga., USA) and denatured at 95° C. for 10 min. An aliquot of total protein (20 μg) were electrophoresed on 12% SDS-PAGE mini gels and were transferred onto PVDF membrane. Membranes were blocked at room temperature with 5% bovine serum albumin (BSA) in Tris-buffered saline Tween-20 (TBST) buffer and probed with targeted primary antibodies overnight at cold room and then blotted with respective secondary antibody. Visualization was performed using BioRad system (Hercules, Calif., USA) with electro-chemiluminescence substrate. Protein level was normalized to the matching densitometric value of internal control.

Statistical Analysis

Statistical analyses were performed by Prism GraphPad software (Chicago, Ill., USA). All experiments have been performed at least three independent times in triplicate. All mean values are presented with the standard deviation. Treatment effects were analyzed using one-way analysis of variance (ANOVA). The differences between groups were tested by Tukey's multiple range tests with $p<0.05$ considered as statistically significant.

Example 1: Preparation of GQDs

GQDs with green fluorescence were synthesized by a one-step chemical oxidation reaction directly from graphite powder. The exemplary synthesis is depicted in FIG. 1. This method takes little time, as fast as 90 minutes, with the photoluminescence quantum yield of 13.1% (quinine sulfate of 0.54 as the reference). Briefly, 60 mg graphite and 180 mg $KMnO_4$ were weighted and added into 18 ml mixed acid (ratio of H2SO4 to HNO3 is 5:1). The mixed solution was heated at 160° C. in a polytetrafluoroethylene-lined (also known as Teflon) autoclave reactor (20 ml) for 90 min. Following the reaction, unreacted KMnO4 and acids were reacted by $H_2O_2$ solution and saturated by $Na_2CO_3$ solution, followed by a 24-h dialysis (cut-off 1,000 Da).

Figure 2:
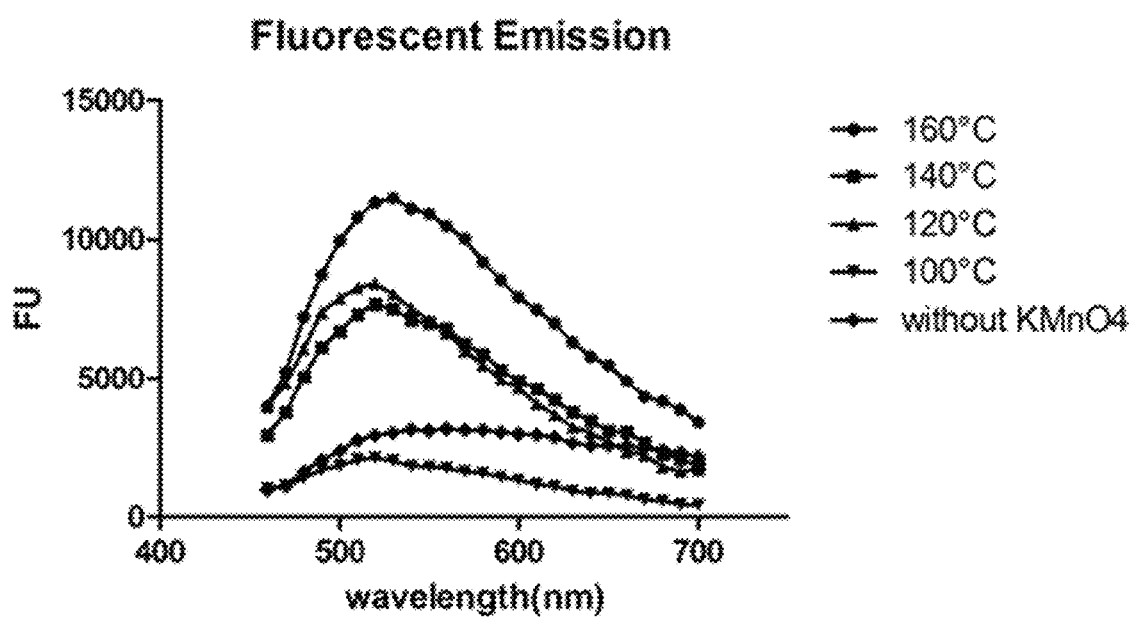
FIG. 2 is a graph of the fluorescence emission spectra of graphene quantum dot production in the presence of $HNO_3$, $H_2SO_4$, and $KMnO_4$ as a function of temperature. The fluorescence emission spectra in the presence of $HNO_3$ and $H_2SO_4$ (without $KMnO_4$) is included as a reference.
Figure 3:
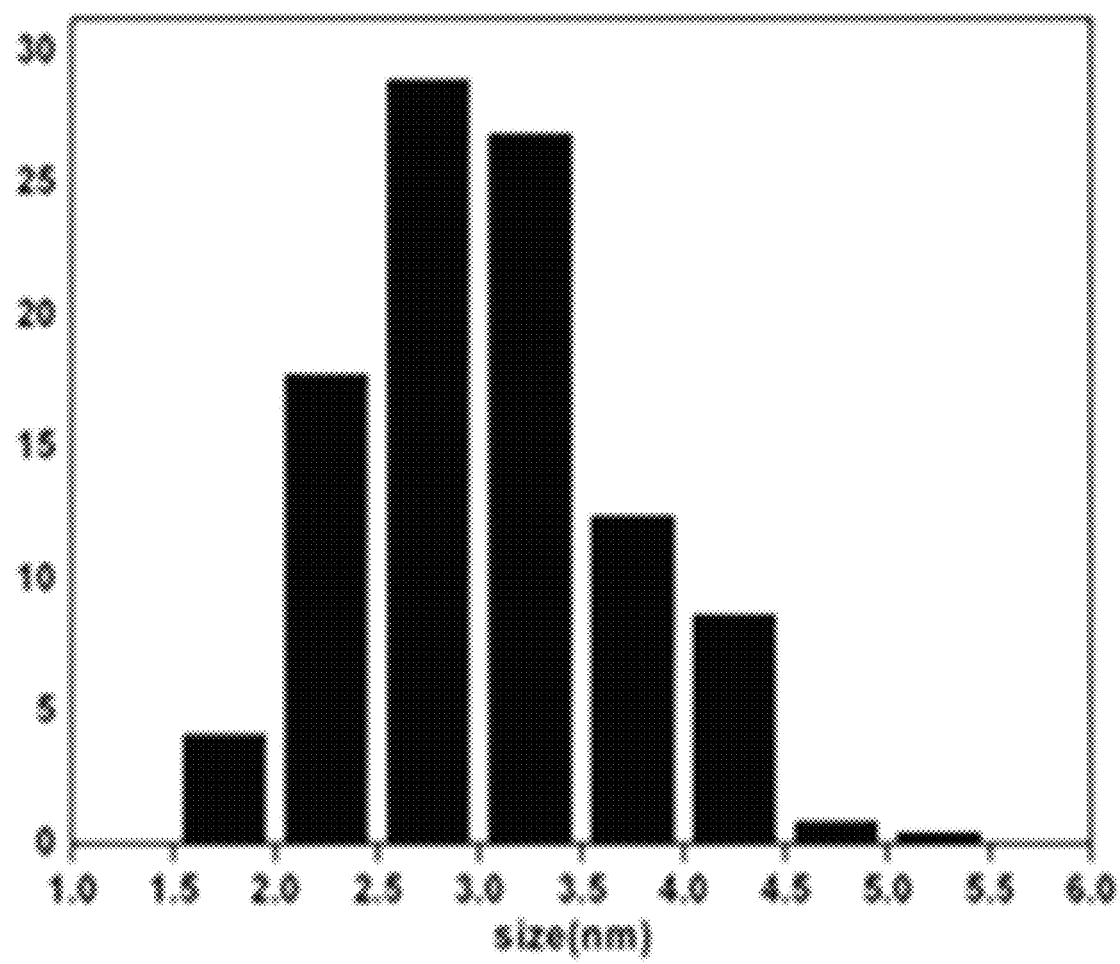
FIG. 3 is a bar graph of the size distribution (%, along the left axis) as a function of the graphene quantum dot diameter (nm, along the bottom axis) depicting the monodisperse size distribution of the graphene quantum dots.

The sizes of the GQDs were evaluated via Transmission Electron Microscopy image and size distribution of GQDs, depicted in FIG. 3, indicates a monodisperse size distribution that has a relatively narrow distribution between 1.5 to 5.5 nm with an average diameter of 3.03 nm. High-resolution TEM (HRTEM) image of the GQD and the corresponding (SAD) pattern indicated the high crystallinity of the GQDs with a lattice parameter of 0.21 nm. Topographic morphology of the GQDs was obtained from Atomic Force Microscope with an average height of about 1 nm. The AFM images demonstrated that most of the GQDs are single or bi-layered, suggesting that all the graphene sheets with multiple layers were tailored into small GQDs sheets by the synergistic interaction of $KMnO_4$, concentrated $H_2SO_4$, and $HNO_3$. In order to confirm the synergistic interaction role of these three oxidants, we performed the reaction on the same condition without $KMnO_4$, or $H_2SO_4$, and $HNO_3$. We carried out a series synthesis reactions at different temperature points and measure the PL behavior of as-synthesized GQDs. The results depicted in FIG. 2 demonstrate the formation of GQDs begins as the temperature is heated above 100° C. When the temperature lower than 100° C. or without $KMnO_4$, the fluorescent emission significantly dropped down.

Figure 4:
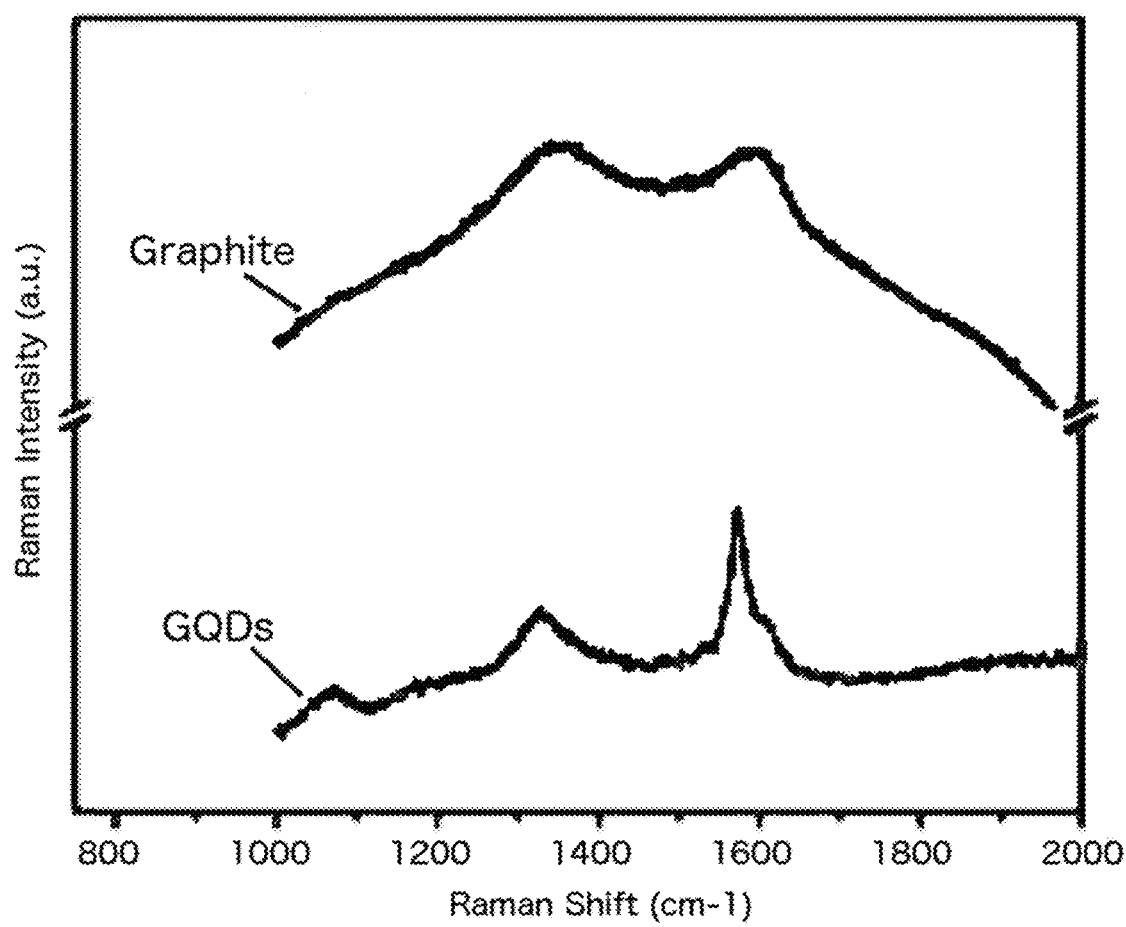
FIG. 4 is a graph of the Raman spectra of graphite (top) and the graphene quantum dots of Example 1 (bottom).
Figure 5:
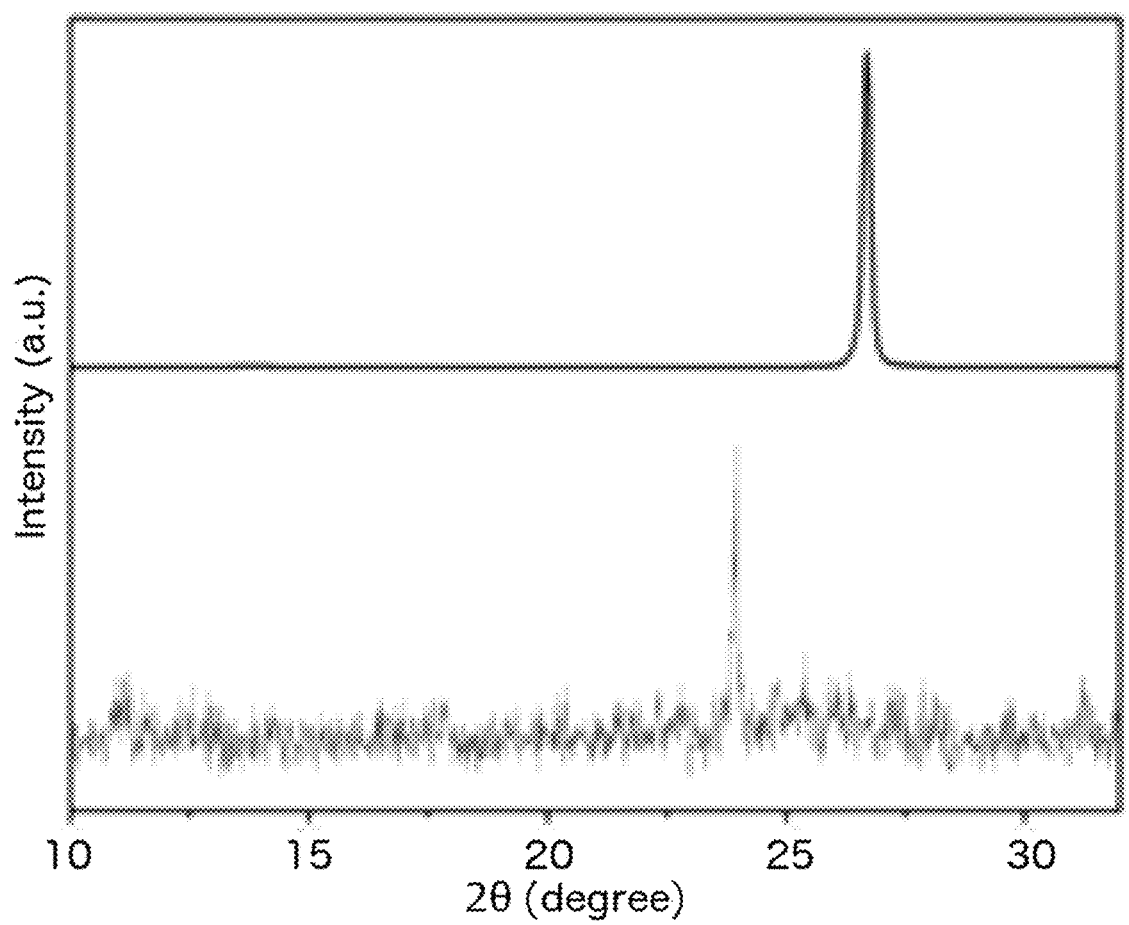
FIG. 5 is a graph of the X-ray diffraction pattern of graphite (top) and the graphene quantum dots of Example 1 (bottom).

Raman spectroscopy was also used to characterize the GQDs. As indicated in FIG. 4, the Raman spectra of GQDs is resolved into two distinctive D and G bands at ~1340 and ~1580 $cm^{-1}$, while that of graphite is at ~1328 and ~1572 $cm^{-1}$. In case of nanocrystalline graphite, the intensity ratio ($I_D/I_G$) is known to inversely proportional to the crystalline grains. This suggests that GQDs are more defective than graphene sheets, possibly due to the dominant contributions from the edge states at the periphery of GQDs. The typical XRD patterns of graphite and the GQDs are presented in FIG. 5. In the case of graphite, its interlayer spacing is 0.335 nm, which is in accordance with previous reports. The interlayer spacing of GQDs, however, expand to 0.372 nm which is determined by Bragg's law $2d \sin\theta = n\lambda$, and a peak (002) centered at 23.87 degree is observed. In comparison with graphite, the XRD peaks for GQDs shifted to a lower degree, revealing a larger interlayer distance than the initial graphite. This is mainly ascribed to the oxygen-containing groups introduced in the exfoliation and oxidation of graphite, leading to the enhancement of interlayer spacing.

Figure 6:
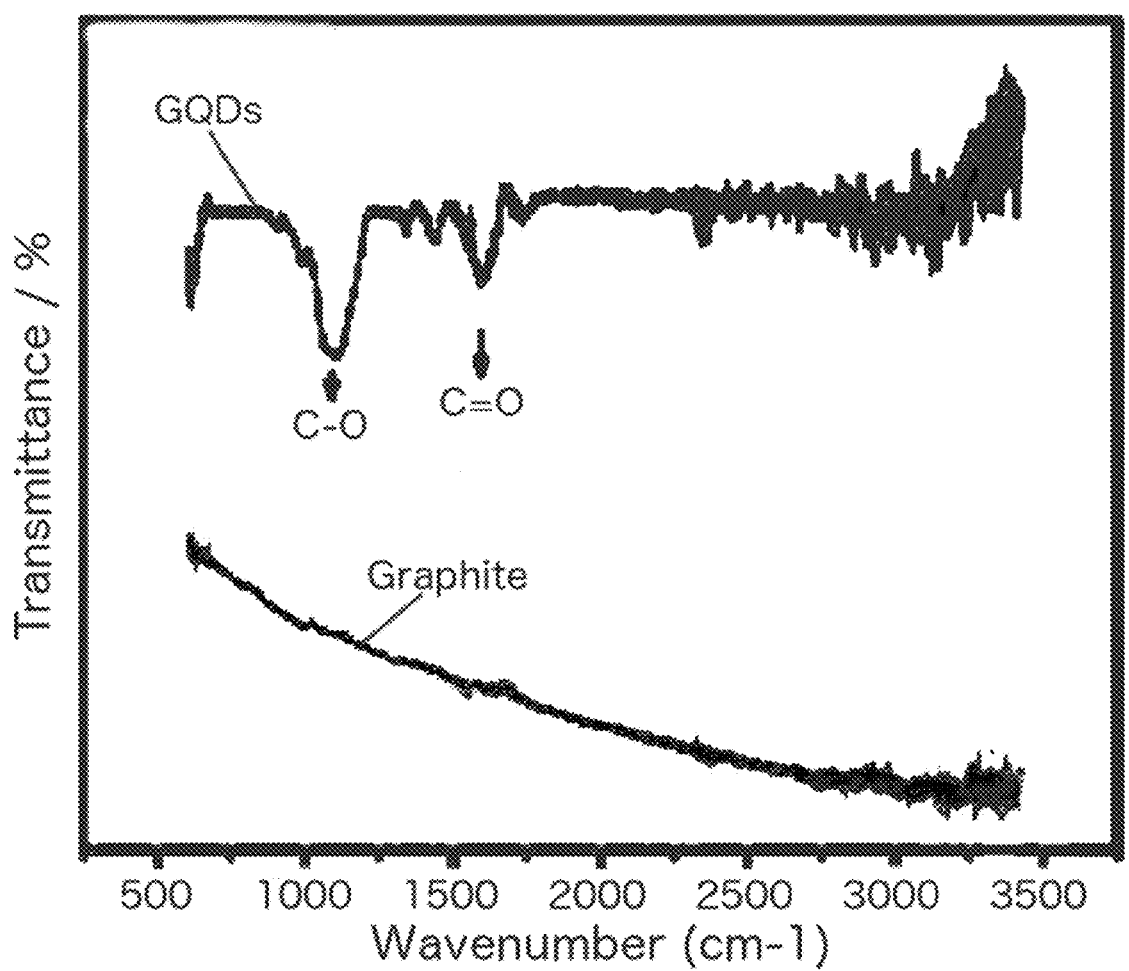
FIG. 6 is a Fourier Transmission Infrared (FTIR) spectrum of graphite (bottom) and the graphene quantum dots of Example 1 (top) depicting the presence of the C—O and C=O stretching modes in the graphene quantum dots.
Figure 7:
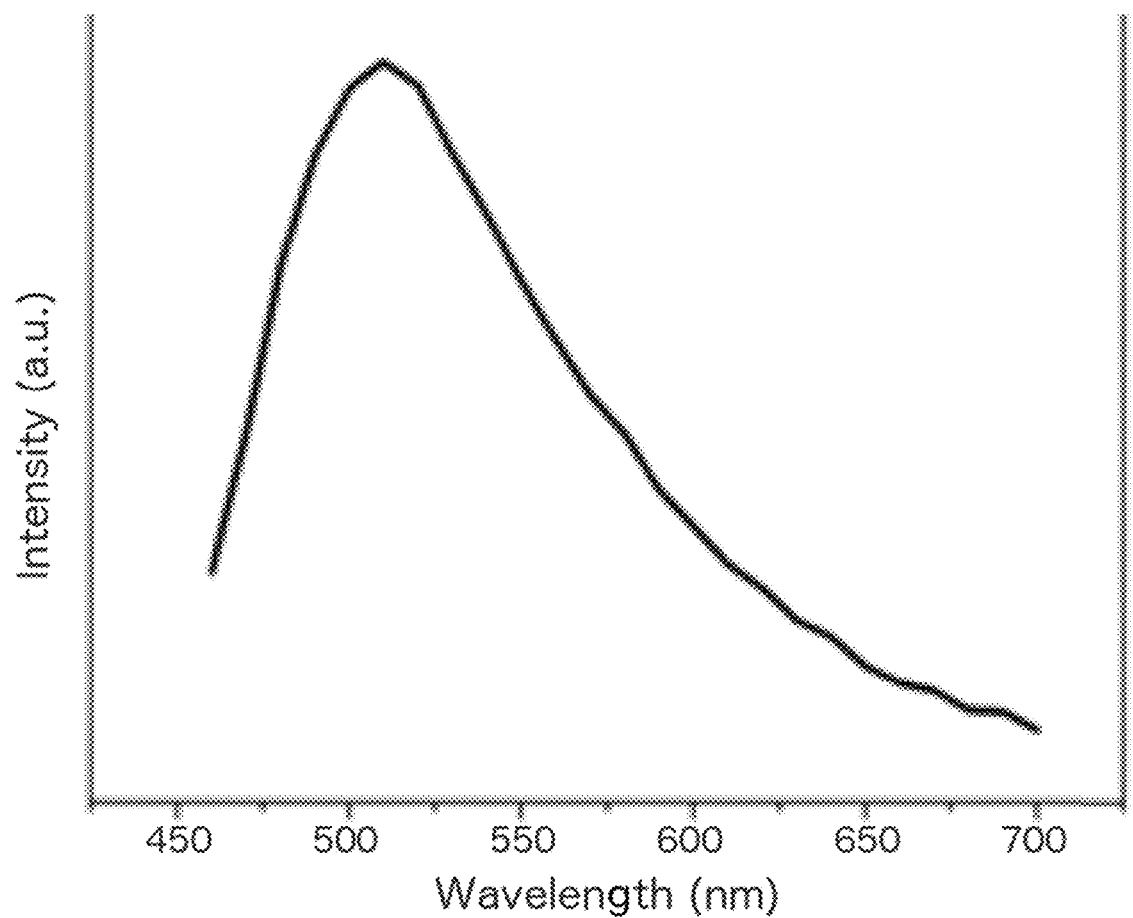
FIG. 7 is a graph of the fluorescence emission spectra of the graphene quantum dots of Example 1 (excited at 440 nm).

As the Fourier transform infrared (FTIR) spectrum in FIG. 6 showed, many chemical groups such as C—O, C═O, were introduced to the edges of GQDs during the oxidation cutting process, which makes GQDs possess excellent solubility in water, PBS, cell culture medium, and many organic solvents. FIG. 7 shows the photoluminescence spectra of GQDs aqueous solution at 440 nm excitation. Like most luminescent carbon nanoparticles, the GQDs also exhibit an excitation-dependent PL behavior. To explore the optical properties of the GQDs, we carried out a detailed PL study by using different excitation wavelengths. The emission peaks of GQDs shift with varying excitation, exhibiting excitation-dependent PL behavior.

Figure 8:
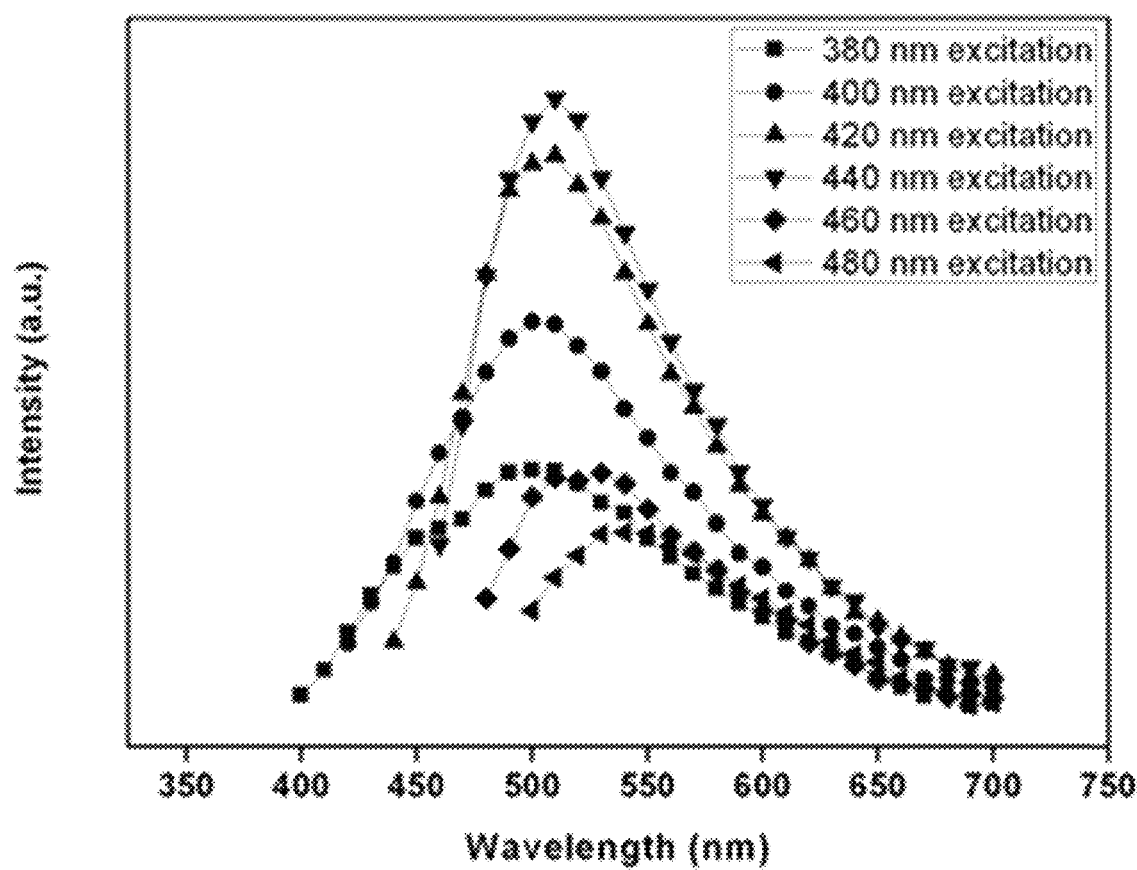
FIG. 8 is a graph of the fluorescence emission spectra of the graphene quantum dots of Example 1 as a function of the excitation wavelength.
Figure 9:
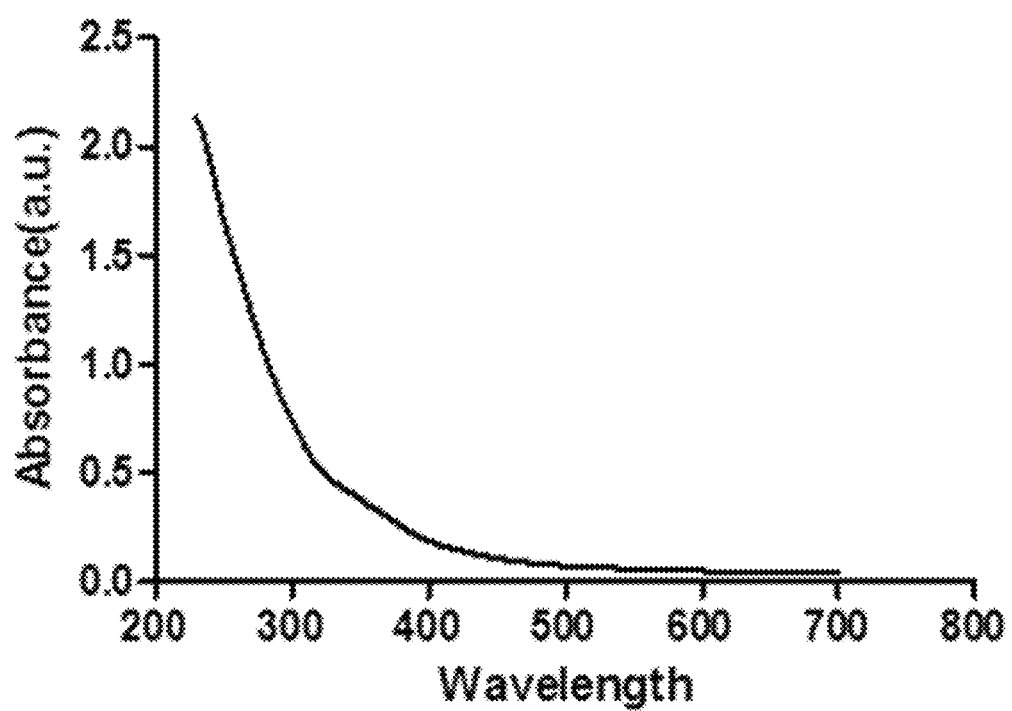
FIG. 9 is a graph of the UV-VIS absorption spectrum of the graphene quantum dots of Example 1.

The emission peak will shift when change the excitation wavelength (As shown in FIG. 8). GQDs irradiated under 365 nm UV light demonstrated green fluorescence visible by naked eye. The UV-visible absorption spectrum is shown as FIG. 12. At 230 nm, there is a strong absorption peak of $\pi \rightarrow \pi^*$ transition of aromatic sp2 domains. Besides, a new absorption shoulder around 350 nm can be observed.

Example 2: Cytotoxity of GQDs

The fluorescence of GQDs prepared in Example 1 was measured in vitro is by confocal microscopy. A choriocarcinoma cancer cell line Jar was incubated with GQDs of Example 1 for 4 hours. The green fluorescence of GQDs was observed in cytosol as compared with the red fluorescence of DRAQ5. Fluorescence microscopy images indicated the GQDs were stable and localized in the cystol.

Figure 10:
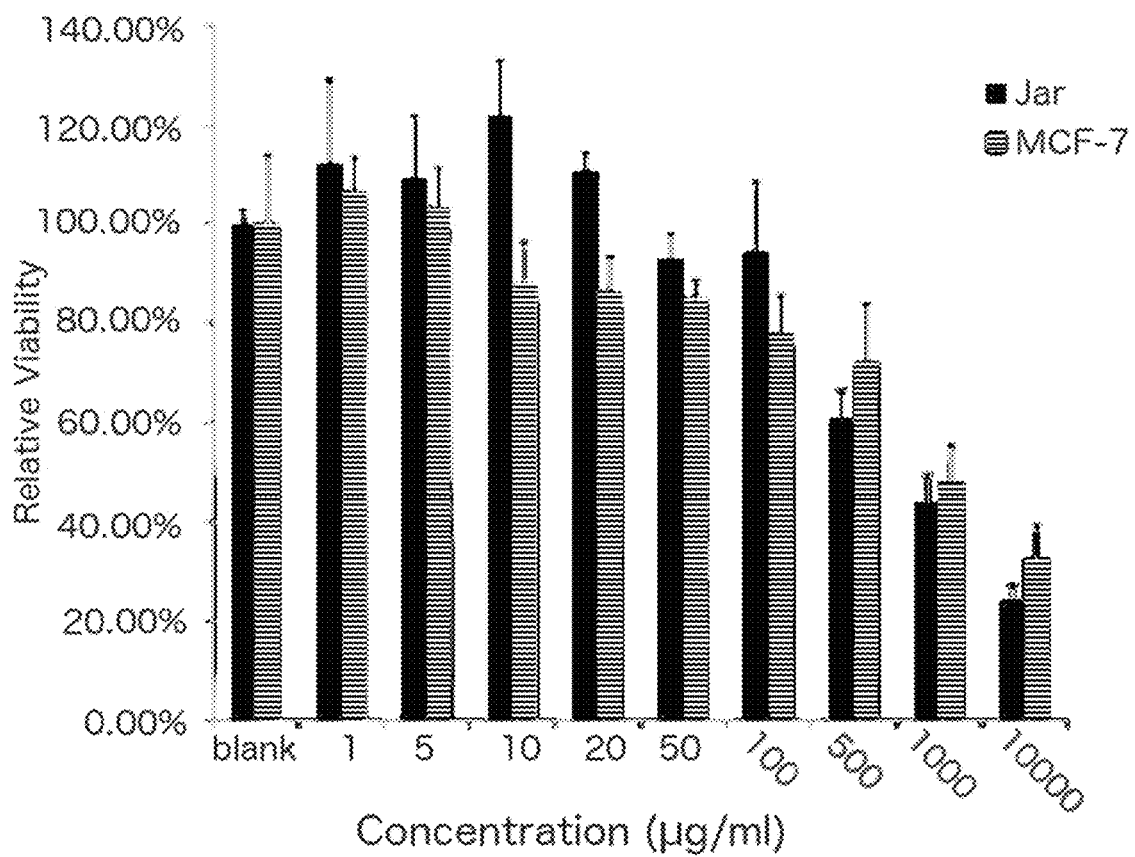
FIG. 10 is a bar graph of the relative cellular viability (% viability) along the left axis as a function of the concentration (μg/ml) of the graphene quantum dots for Jar cells and for MCF-7 cells. For each concentration along the bottom axis the left bar is the relative viability for the Jar cells and the right bar is the relative viability for the MCF-7 cells.

To test the cytotoxicity of GQDs, the choriocarcinoma cancer cell line Jar and breast cancer cell line MCF-7 was incubated for 24 hours with different concentrations of GQDs from Example 1. The results in FIG. 10 demonstrate the cells remained viable at concentration up to at least 100 µg/ml. Up to a GQD concentration of 100 µg/ml, the relative viability of Jar cells is higher than 90% and the relative viability of MCF-7 cells is higher than 80%, demonstrating that GQDs possess relatively low cytotoxicity and high biocompatibility.

Example 3. Conjugating Folic Acid to GQDs

Figure 11:
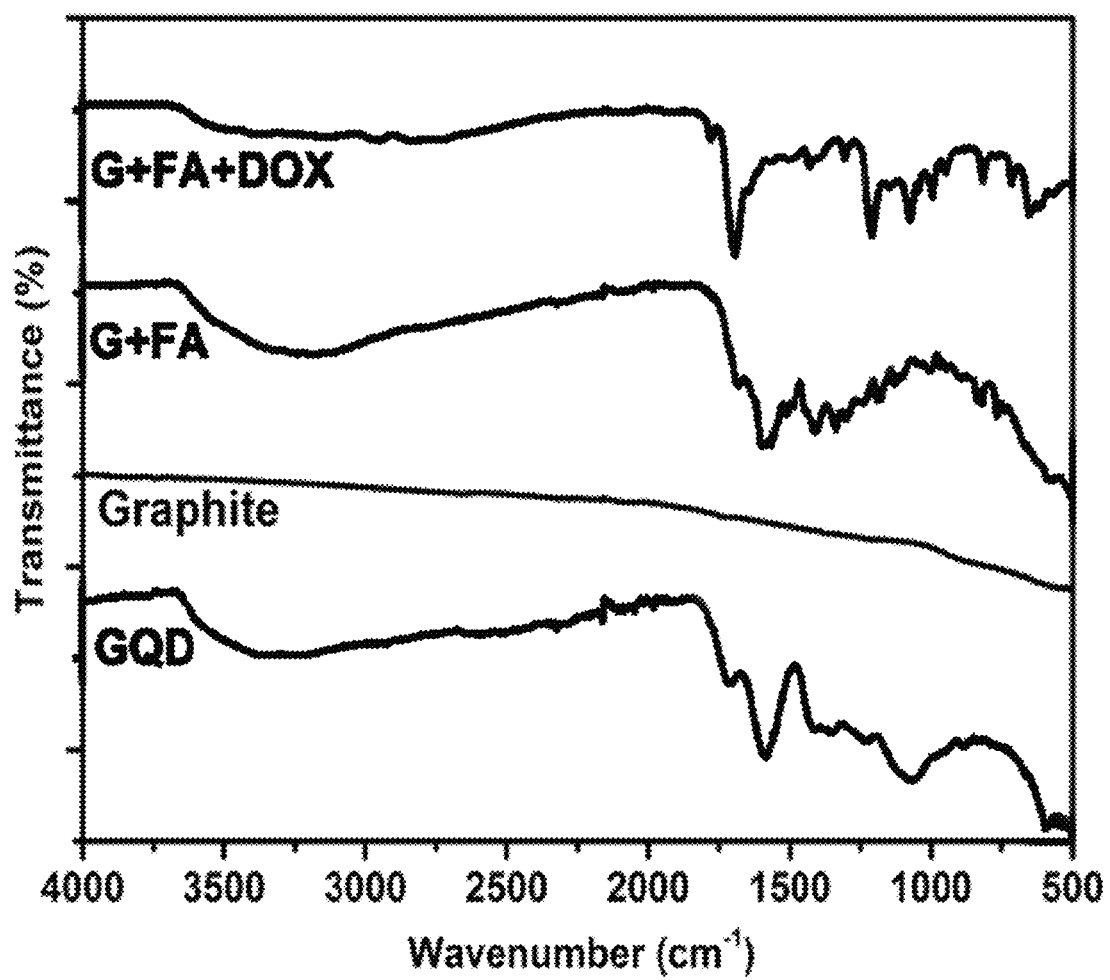
FIG. 11 is an FTIR spectra of the graphite carbon source, the graphene quantum dot (GQD) from example 1, the conjugate of the graphene quantum dot with the folic acid targeting ligand (G+FA), and the Doxorubicin loaded graphene quantum dots with folic acid targeting ligand (G+FA+DOX).
Figure 12:
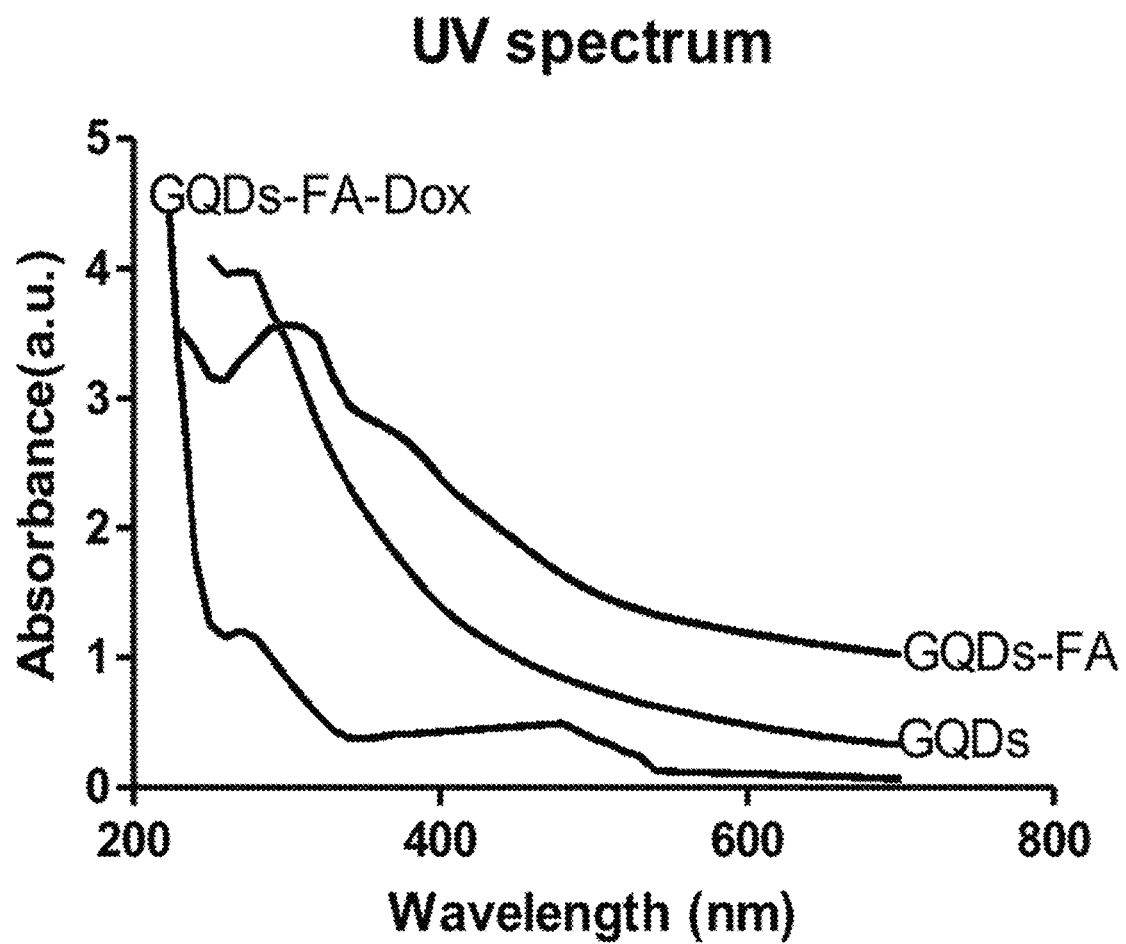
FIG. 12 is a UV absorption spectra of the graphene quantum dots (GQDs), the graphene quantum dot with the folic acid targeting ligand (GQDs-FA), and the Doxorubicin loaded graphene quantum dots with folic acid targeting ligand (GQDs-FA-DOX).

The GQDs from Example 1 were reacted with ammonium hydroxide and hydrogen peroxide to introduce amine reactive coupling groups at the GQD defect sites. The targeting ligand, folic acid (FA), was conjugated to the —$NH_2$ on the edge of GQDs by coupling with crosslinking agents, N-hydroxysuccinimide (NHS) and 1-Ethyl-3-(3-dimethylaminopropyl)-carbodiimide (EDC) at room temperature mixing overnight to produce a GQD-FA conjugate. FIG. 12 shows the UV spectra of GQDs before and after conjugation with FA that there will be a shift peak to 270 nm after conjugation. FTIR spectra showed in FIG. 11 also demonstrates the successful conjugation The conjugation of GQDs with FA and Dox were modified and performed by following the previous described. In brief, synthesized GQDs was reacted with NHS and EDC in DMSO buffer for 30 min with sonication, followed by adding FA stirring over night. The solution was repeatedly dialyzed using dialysis membrane tubing (cut-off 1,000 Da) for 28 h. Dox (200 µl of different concentration from 100, 200, 300, 400, 500 µg/ml Dox solution) was loaded on GQDs (1 ml of 1 mg/ml) via π-π stacking in DMSO solution stirring for 4 h. Then centrifuge the mixture at 12,000 g for 30 min. The pellet is kept as the products of GQDs-FA-Dox. The free Dox was remained in supernatant and the absorption of at 480 nm was measured to calculate the free drug content. The drug loading efficiency was calculated based on the following equation: drug loading (%)=((weight of drug added−weight of free drug in the bath solution)/weight of carriers)×100. The release of DOX from GQD-FA was monitored in PBS buffer at 24 h and 48 h, respectively. And the absorption of at 480 nm was measured to calculate the free drug content The morphology characterization of GQDs was carried out using transmission electron microscopy (TEM, JEM 100CX), high-resolution transmission electron microscopy (HRTEM, Tecnai F20), and Fourier Transform Infrared Spectroscopy (FTIR, PerkinElmer spectrum 100 series).

The synthesized GQDs-FA-DOX had a relative narrow size distribution which was between 10-12 nm as was observed in the TEM image. The FIG. 11 showed the FTIR spectra results for the GQDs, GQDs-FA, and GQDs-FA-DOX. The GQDs only have —C=O, —C—O groups on the edge, while the GQDs-FA have n the FTIR, new peaks at 1271 and 1560 cm-1 appear after conjugation with FA, which are assigned to C—N and N—H stretching, respectively. The new broad peak in the 3300-3500 cm-1 region corresponds to the N—H vibration. In addition, characteristic amide-carbonyl (—NH—CO—) stretching vibration is observed at 1643 cm-1, which implies the formation of amide groups in GQD-FA. The fluorescence of GQD is slightly reduced after the conjugation of FA due to the changes of the chemical groups.

Figure 13:
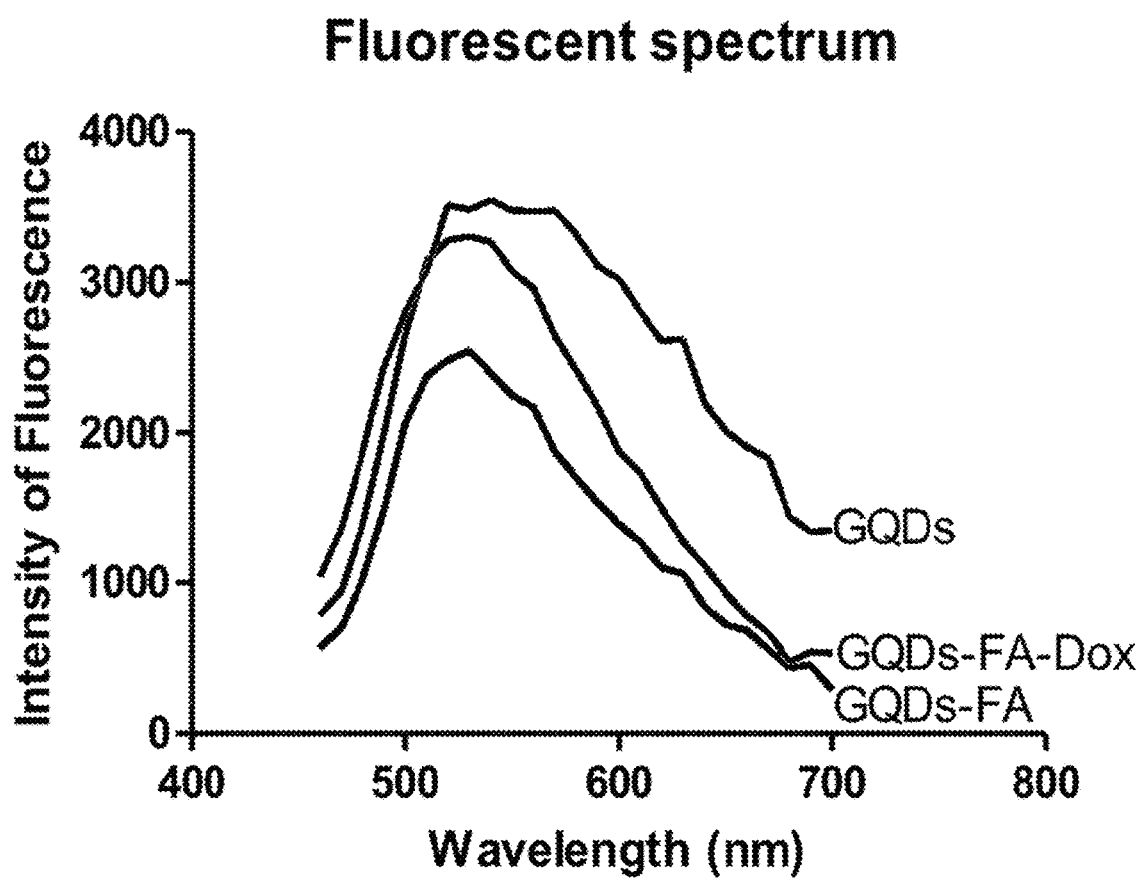
FIG. 13 is an optical fluorescence spectrum of graphene quantum dots (GQDs), the graphene quantum dot with the folic acid targeting ligand (GQDs-FA), and the Doxorubicin loaded graphene quantum dots with folic acid targeting ligand (GQDs-FA-DOX).

In addition, the photoluminescence behavior of GQDs, GQDs-FA, and GQDs-FA-Dox. were examined as shown in FIG. 13. The UV-visible absorption spectrum is shown in FIG. 12. At 230 nm, there was a strong absorption peak indicating π→π* transition of aromatic $sp^2$ domains of GQDs. After conjugated with FA, GQDs-FA showed a new peak that appears at 280 nm after conjugation. The doxorubicin has a strong absorbance around 480 nm, which can be observed in GQDs-FA-Dox.

Example 4. Drug Loading and Releasing

Figure 14:
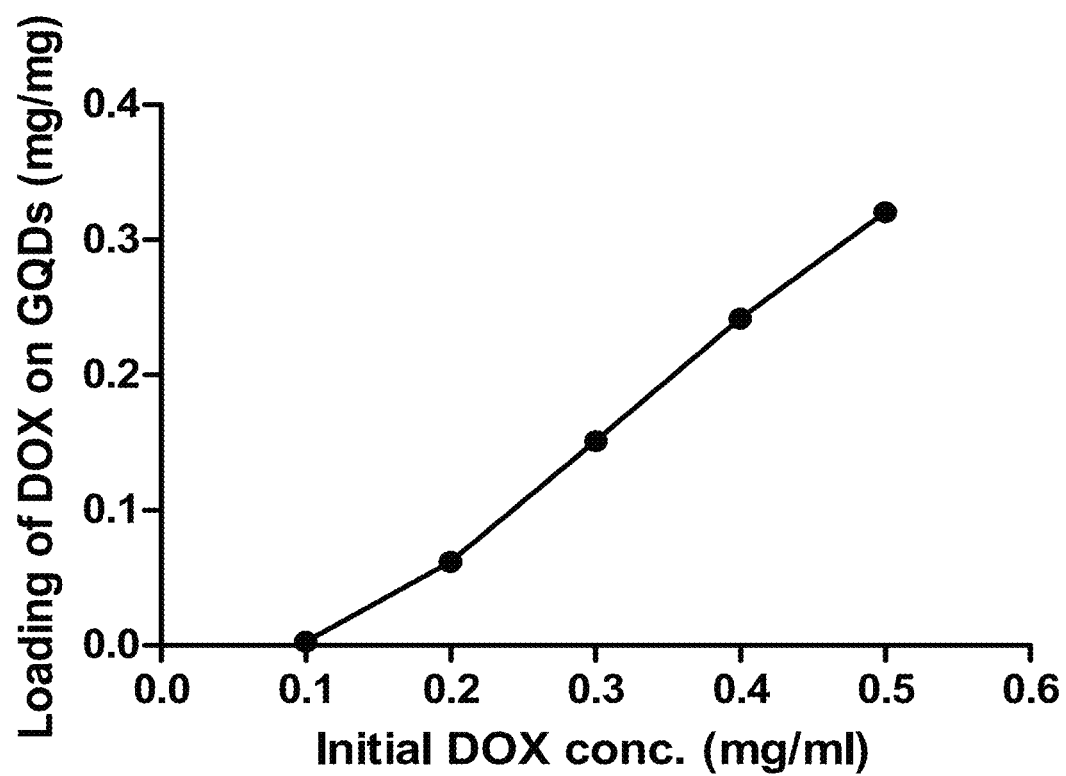
FIG. 14 is a graph of the loading of Doxorubicin (mg/mg) onto the graphene quantum dot with the folic acid targeting ligand (GQDs-FA) as measured based on the absorbance of Doxorubicin at 480 nm as a function of the initial Doxorubicin concentration (mg/ml).
Figure 15:
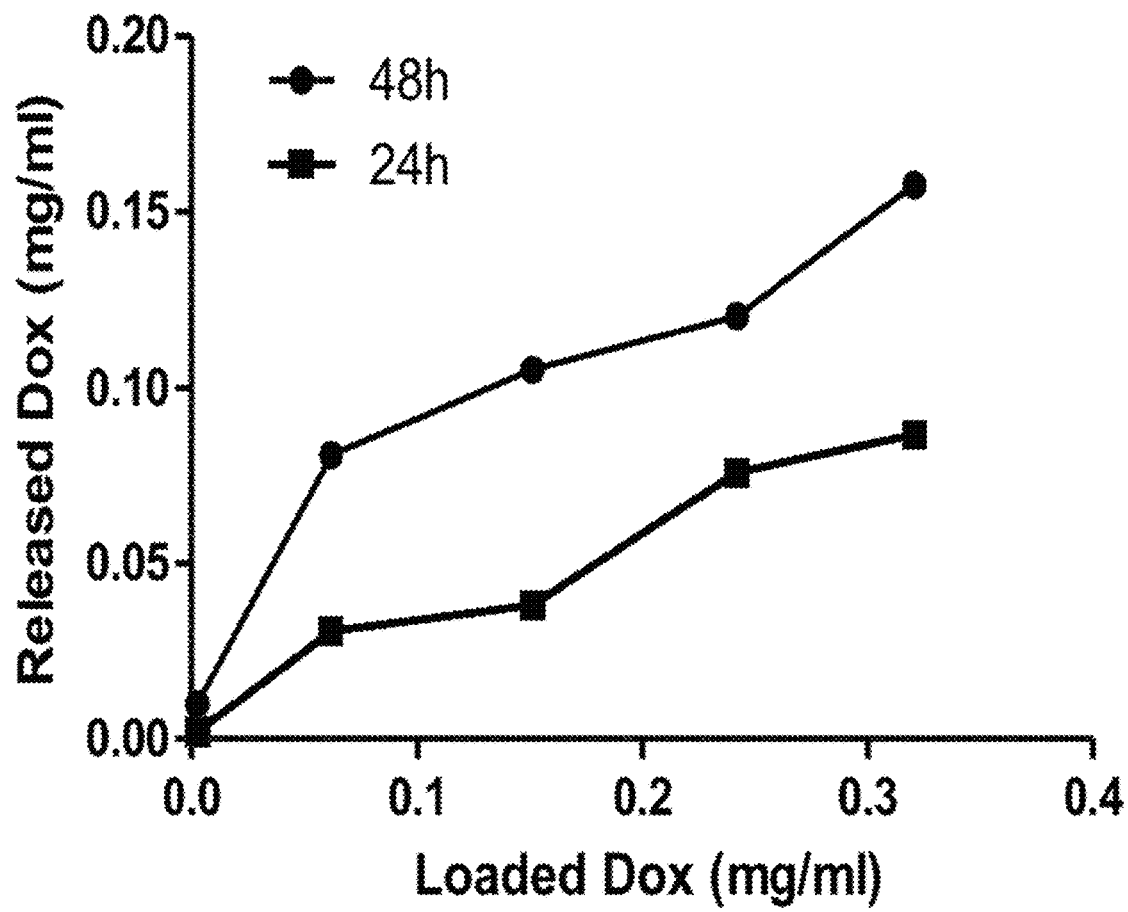
FIG. 15 is a graph of the release of Doxorubicin (mg/ml) at 24 hours (squares) and 48 hours (circles) for Doxorubicin loaded graphene quantum dots with folic acid targeting ligands (GQDs-FA-DOX) as a function of the initial Doxorubicin loading (mg/ml).

The quantification of Dox loading was measured based on the absorbance of Dox at 480 nm. As shown in FIG. 14, the maximum loading capacity of Dox on GQDs-FA was achieved at 64% when the loading ratio of Dox to GQDs-FA was 1:2. The release of Dox from GQD-FA was monitored in cell culture medium at 24 h and 48 h, respectively. The drug releasing of GQD-FA-Dox is in a time-dependent manner. 48 h of releasing can reach up to 50% releasing of Dox (FIG. 15).

Example 5. Uptake of GQDs-FA-Dox by Ovarian Cancer & Normal Epithelial Cells

Figure 16:
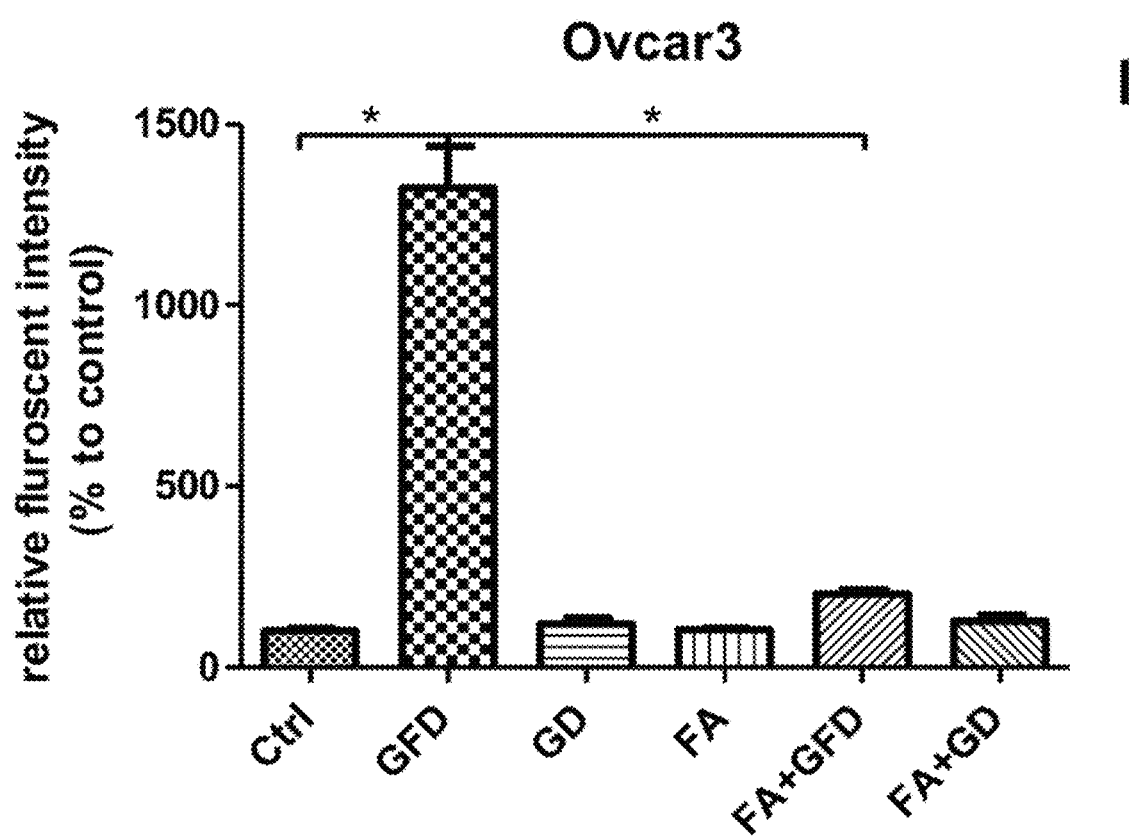
FIG. 16 is a bar graph of the uptake (increase fluorescence intensity, % relative to control) in Ovcar3 cells for the control (ctrl), the Doxorubicin loaded graphene quantum dots with folic acid targeting ligand (GFD), the Doxorubicin loaded graphene quantum dot without the folic acid targeting ligand (GD), free folic acid (FA), the Doxorubicin loaded graphene quantum dots with folic acid targeting ligand in the presence of excess free folic acid (FA+GFD), and the Doxorubicin loaded graphene quantum dot without the folic acid targeting ligand in the presence of excess free folic acid (FA+GD).
Figure 17:
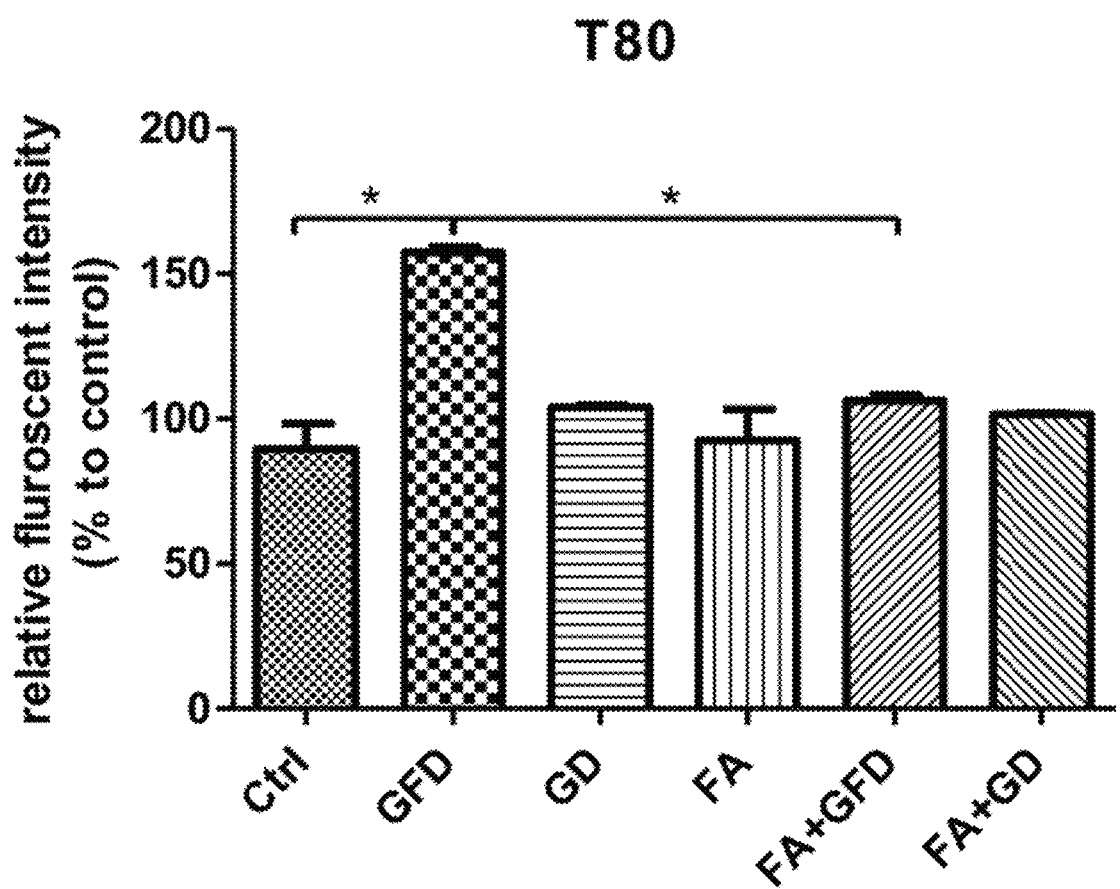
FIG. 17 is a bar graph of the uptake (increase fluorescence intensity, % relative to control) in T80 ovarian surface epithelial cells for the control (ctrl), the Doxorubicin loaded graphene quantum dots with folic acid targeting ligand (GFD), the Doxorubicin loaded graphene quantum dot without the folic acid targeting ligand (GD), free folic acid (FA), the Doxorubicin loaded graphene quantum dots with folic acid targeting ligand in the presence of excess free folic acid (FA+GFD), and the Doxorubicin loaded graphene quantum dot without the folic acid targeting ligand in the presence of excess free folic acid (FA+GD).

The uptake of GQDs-FA-Dox and GQDs-Dox were quantified by H4 microplate reader in FIG. 16 The GQDs-FA-Dox has a 13.2-fold increasing of fluorescence than the control groups by Ovcar3 cells (FR overexpressed). With the inhibition of FR by adding excessively folic acid, the fluorescence of GQDs-FA-Dox in cells was significantly dropped. The GQDs-Dox without conjugation of FA also gave the relatively low fluorescent signal. Those results indicated that the uptake of GQDs-FA-Dox requires the involvement of FR and FA. The uptake of GQDs-FA-Dox by T80 ovarian surface epithelial cells (FR negative) also increased the fluorescent signal by 1.6-fold compared to the control groups (FIG. 17), but this increasing is much less than that of the FR overexpressed ovcar3 cells.

The uptake of GQDs-FA-Dox by ovcar3 cells was also confirmed using the confocal laser microscope. Hoechst 33342 was used to stain the nucleus of ovcar3 cells. GQDs staining indicated localization of GQDs in cytosol. While Dox staining was relatively low iand localized in cytosol, instead of nucleus, this was likely due to the incubation time of this study is 1 h, while the releasing of Dox is relatively low that most Dox remains on the GQDs-FA without entering the nucleus.

Example 6. Effect of GQDs-FA-Dox on Cellular Viability

Figure 18:
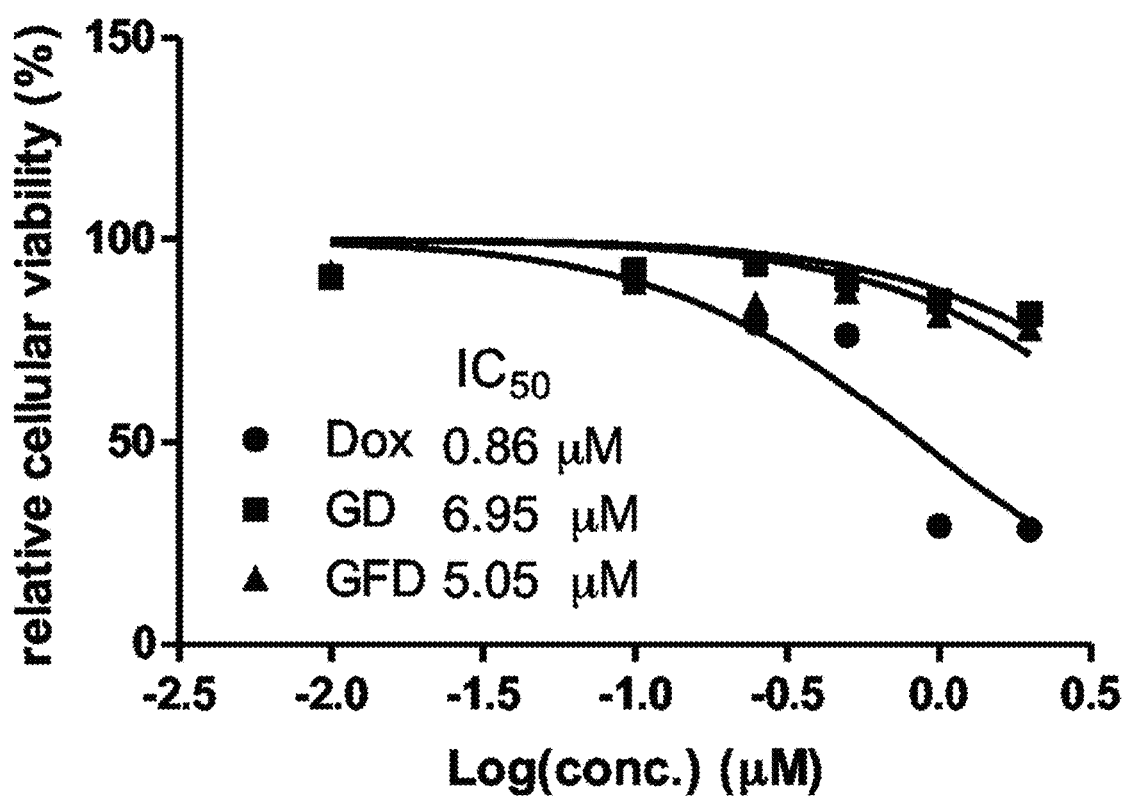
FIG. 18 is a graph of the relative cellular viability (%) of T80 ovarian surface epithelial cells as a function of the log of the concentration (μM) for Doxorubicin (Dox), Doxorubicin loaded graphene quantum dots (GD), and the Doxorubicin loaded graphene quantum dots with folic acid targeting ligand (GFD). The $IC_{50}$ values are provided for each.
Figure 19:
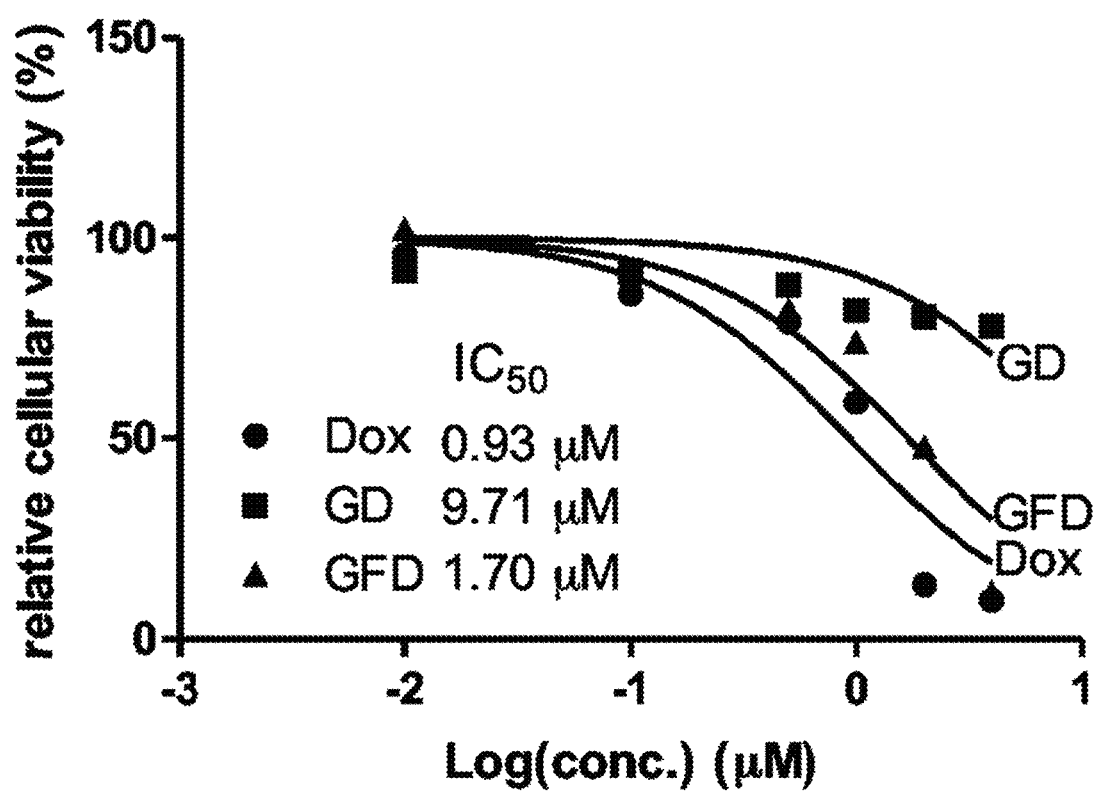
FIG. 19 is a graph of the relative cellular viability (%) of Ovcar3 cells as a function of the log of the concentration (μM) for Doxorubicin (Dox), Doxorubicin loaded graphene quantum dots (GD), and the Doxorubicin loaded graphene quantum dots with folic acid targeting ligand (GFD). The $IC_{50}$ values are provided for each.

To determine the effective dosage of GQDs-FA-Dox on ovarian cancer cells and normal cells, a dose-course MTT assay was done on Ovcar3 cells. The cells were treated with a series of concentration of DOX, GQDs-FA-Dox, and GQDs-Dox for 0.01 to 4 µM (equivalent to Dox concentration) for 24 h. The cell relative viability possesses statistic significance between the groups with or without FA to different cell lines with or without FR. As shown in FIG. 18, the $IC_{50}$ of DOX, GQDs-FA-Dox, and GQDs-Dox to normal ovary epithelial cells T80 was 0.86, 5.05, and 6.95 µM. While $IC_{50}$ of DOX, GQDs-FA-Dox, and GQDs-Dox to ovarian cells Ovcar3 was 0.93, 9.71, and 1.70 µM (FIG. 19). The $IC_{50}$ by GQDs-FA-Dox to Ovcar3 cells significantly decreased comparing to that of GQDs-Dox due to the FR of ovcar3 cells more easily uptake the GQDs-FA-Dox. While without the FR, it makes no difference for T80 cells to uptake the GQDs-FA-Dox or GQDs-Dox. This finding confirmed the better efficacy of the GQDs-FA-Dox to FR overexpressed ovarian cancer cells than GQDs-Dox to FR overexpressed ovarian cancer cells or the GQDs-FA-Dox and GQDs-Dox to FR negative ovary cells.

Figure 28:
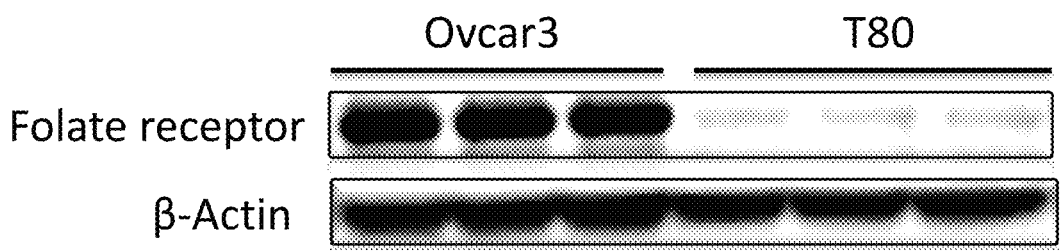
FIG. 28 is a picture of the western blotting analysis of folate receptor (FR) expression in ovarian cancer cells ovcar3 and ovarian surface epithelial cells T80.

Western blotting analysis of folate receptor expression in ovarian cancer cells ovcar3 and ovarian surface epithelial cells T80 were performed (FIG. 28). The results indicated that varian cancer cells ovcar3 overexpressed the folate receptor while ovarian surface epithelial cells T80 has very low expression level of folate receptor. This data confirmed our study model as ovcar3 (FR+) and T80 (FR−).

Colony formation assays were performed with ovarian cancer cells ovcar3 and ovarian surface epithelial cells T80 to examine the impact of DOX, GQDs, GQDs-FA-Dox, or GQDs-Dox on the cell growth inhibition. GQDs-FA-Dox and DOX strongly inhibited the colony growth of ovarian cancer cells ovcar3, While GQDs-FA-Dox has no significant effect on colony growth in ovarian surface epithelial cells T80. These data suggesting that GQDs-FA-Dox could be used for ovarian cancer treatment. Folic acid provides an protective effect to the ovcar3 cells in response of GQDs-FA-DOX, which may due to the blocking effect of folic acid to the folate receptor.

Figure 20:
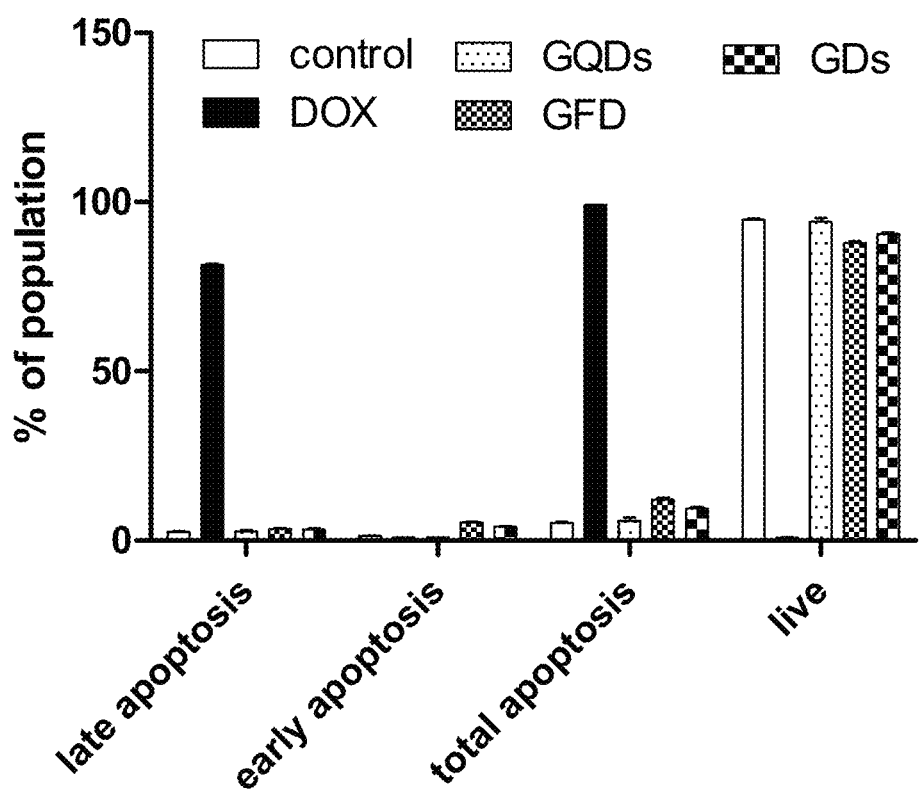
FIG. 20 is a bar graph of the cellular apoptosis quantified by flow cytometric analysis (% of population) exhibiting late apoptosis, early apoptosis, total apoptosis, and live T80 ovarian surface epithelial cells for the control group and after addition of graphene quantum dots (GQDs), free Doxorubicin (DOX), Doxorubicin loaded graphene quantum dots (GDs), and Doxorubicin loaded graphene quantum dots with folic acid targeting ligand (GFD).
Figure 21:
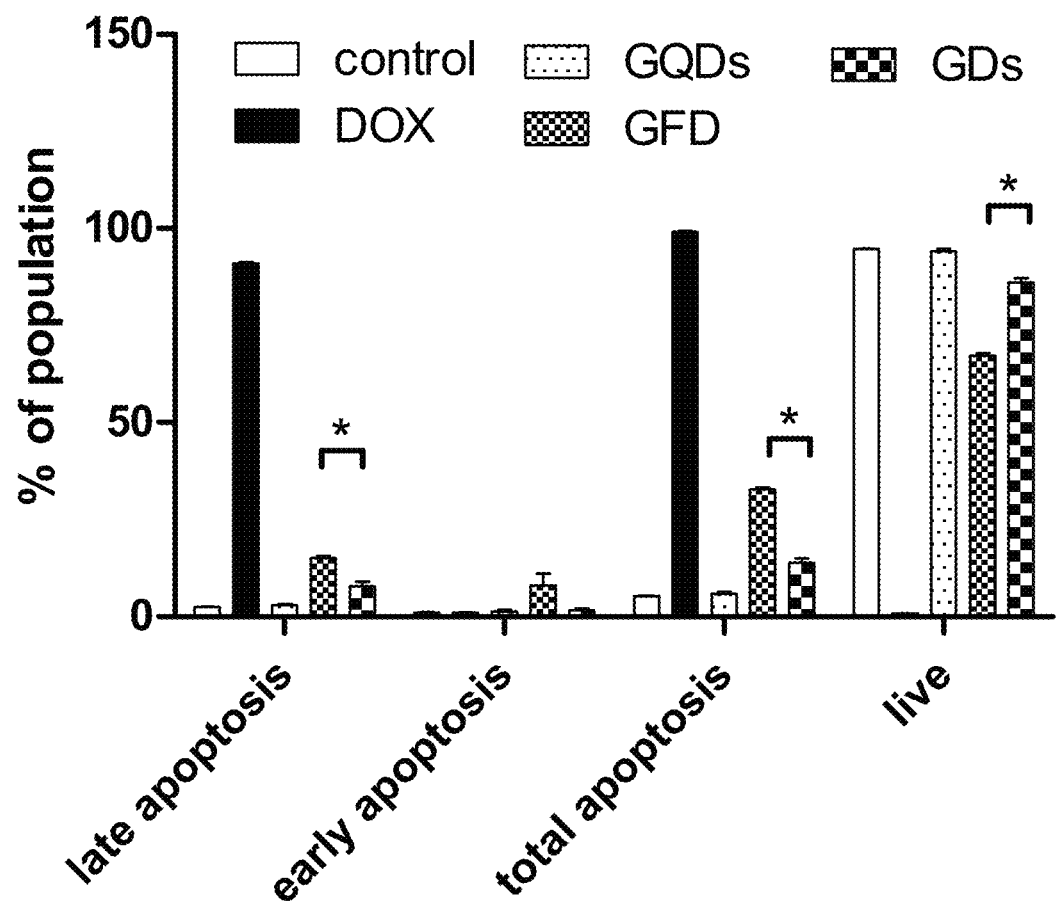
FIG. 21 is a bar graph of the cellular apoptosis quantified by flow cytometric analysis (% of population) exhibiting late apoptosis, early apoptosis, total apoptosis, and live Ovcar3 cells for the control group and after addition of graphene quantum dots (GQDs), free Doxorubicin (DOX), Doxorubicin loaded graphene quantum dots (GDs), and Doxorubicin loaded graphene quantum dots with folic acid targeting ligand (GFD).

Example 7. Apoptosis Effect of GQDs-FA-Dox on Ovarian Cancer & Normal Epithelial Cells To further examine the anti-cancer effect of GQDs-FA-Dox on ovarian cancer cells, the effect of GQDs-FA-Dox and GQDs-Dox on cellular apoptosis was quantified by flow cytometric analysis. The number of apoptotic cells without GQD treatment was 3-5.0% (early+late apoptosis) (FIG. 20 and FIG. 21). Non-treated group or GQDs treated group has no difference in both T80 (FIG. 20) cells and Ovcar3 (FIG. 21) cells, which indicated that the non-apoptotic toxicity of GQDs on both cell lines. Similar to the cellular viability assay, the apoptotic effect of the GQDs-FA-Dox to FR overexpressed ovarian cancer cells Ovcar3 is much more stronger than GQDs-Dox to FR overexpressed ovarian cancer cells or the GQDs-FA-Dox and GQDs-Dox to FR negative ovary cells.

Example 8. Effect of GQDs on Epithelial-Mesenchymal Transition (EMT)

Figure 22:
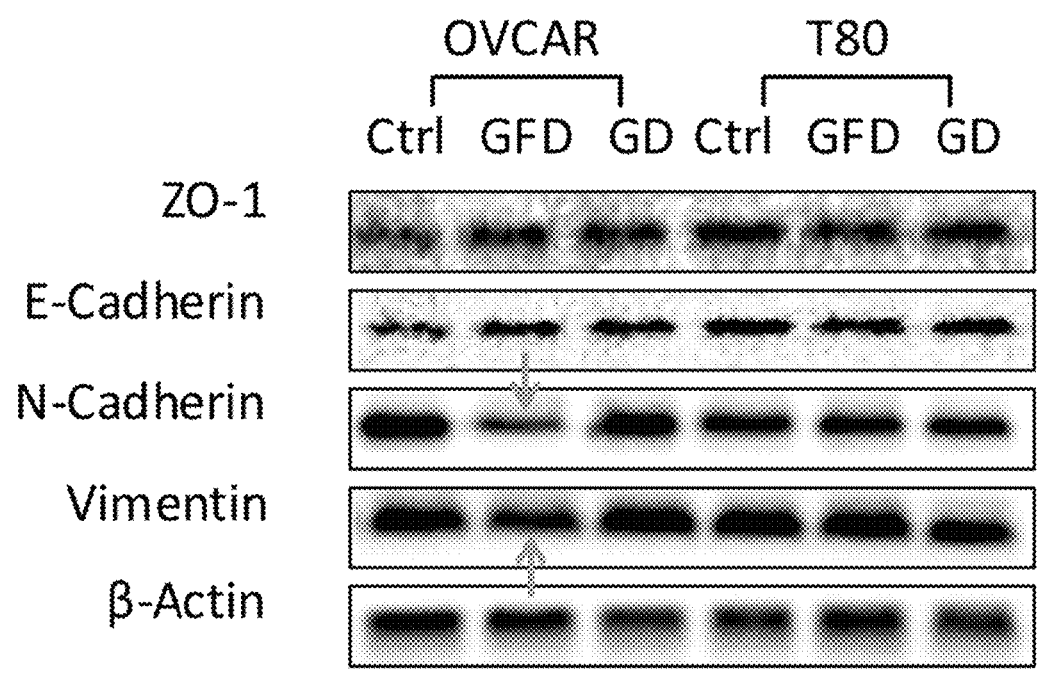
FIG. 22 is a picture of the western blotting analysis of key epithelial-mesenchymal transition (EMT) markers in ovarian cancer cells ovcar3 and ovarian surface epithelial cells T80 after being treated with or without Doxorubicin loaded graphene quantum dots with folic acid targeting ligands (GFD) and Doxorubicin loaded graphene quantum (GD).

EMT is a key step of cancer invasion by losing their epithelial morphology and undergoing migratory behavior. To further explore the anti-cancer effect GQDs-FA-Dox, we examined the effect of GQDs on the expression levels of several key EMT markers in ovarian cancer cells ovcar3 and ovarian surface epithelial cells T80. When the skove3 cells were treated with GQDs-FA-Dox, the expression of N-cadherin and Vimentin were only slightly reduced (FIG. 22). These two molecules are biomarkers of the mesenchymal cell morphologies. Thus, it indicated that the GQDs-FA-Dox has an effect on inhibit the EM of ovarian cancer, while the GQDs-Dox does not have any obvious effects on ovarian cancer. The EMT behavior of normal cells T80 was not affected significantly. On the one hand, it might be that the GQDs-FA-Dox was difficulty to enter the T80 cells due to the little expression of FR. On the other hand, the T80 is not the tumor cells, which indicates that it does not possess high potential in EMT.

Example 9. GQDs-FA-Dox Reduced Immunotoxicity and Cardiotoxicity

Figure 23:
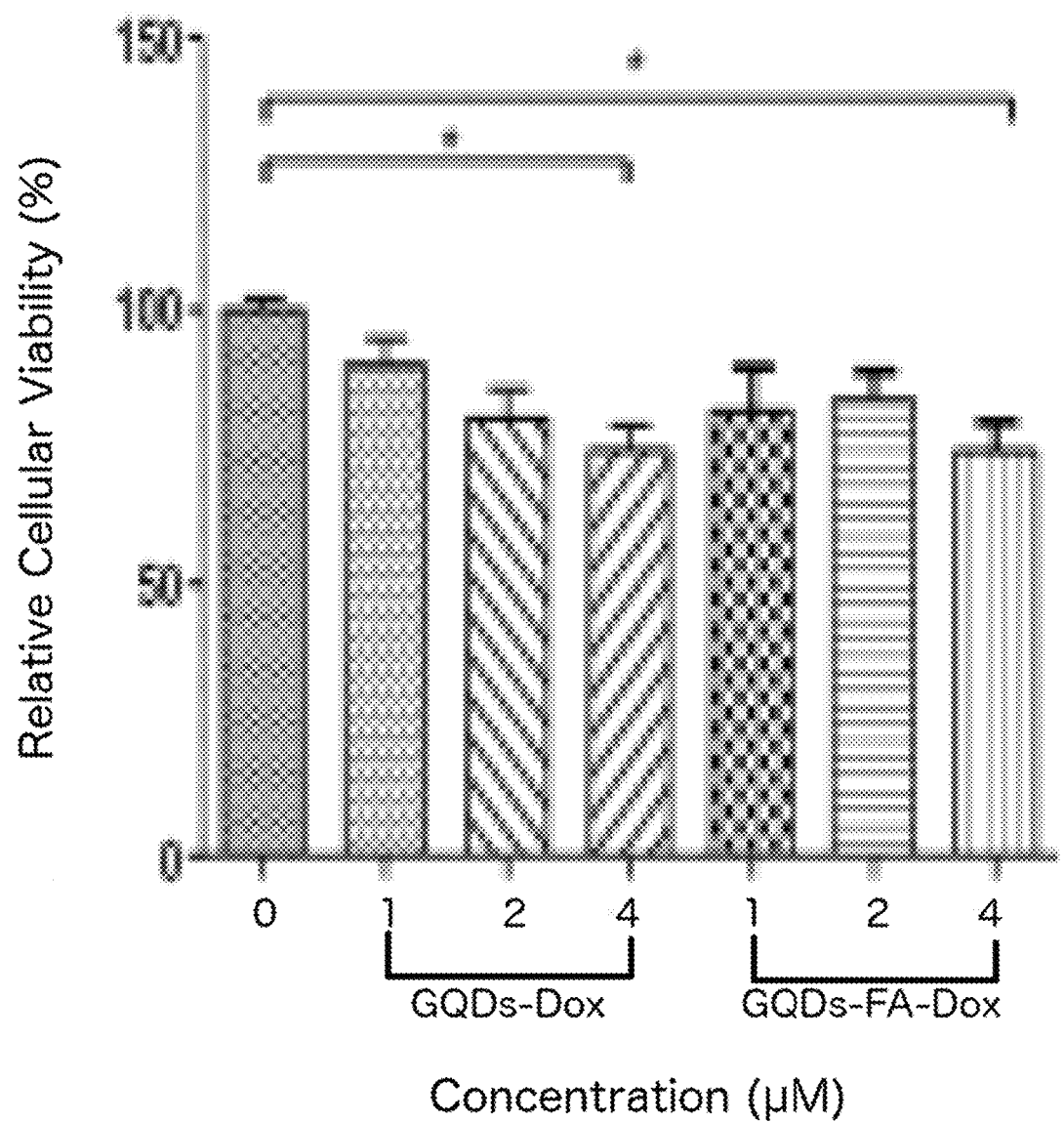
FIG. 23 is a bar graph of the cellular relatively viability (%) of PMA-activated THP-1 cells after being treated with or without Doxorubicin loaded graphene quantum dots with folic acid targeting ligands (GQDs-FA-DOX) and Doxorubicin loaded graphene quantum dots (GQDs-Dox) at concentrations of 1, 2, and 4 µm.
Figure 24:
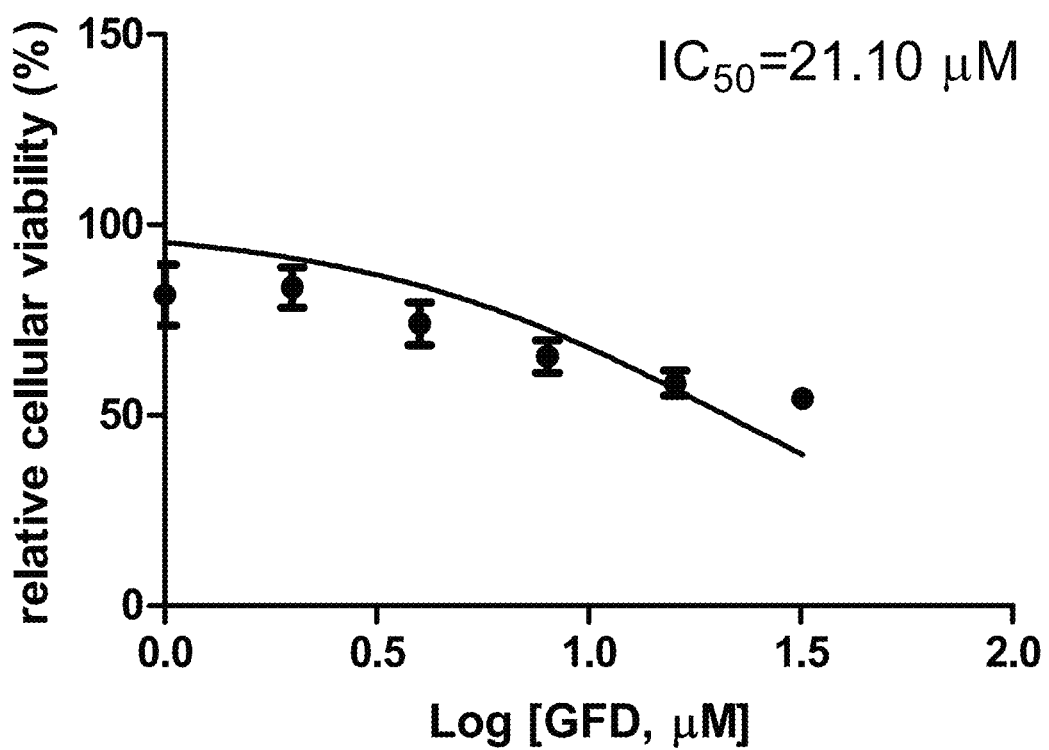
FIG. 24 is a graph of the relative cellular viability (%) of PMA-activated THP-1 macrophages as a function of the Log concentration (µm) of Doxorubicin loaded graphene quantum dots with folic acid targeting ligands (GFD), indicating relative low immunotoxicity induced by GFD and an $IC_{50}$ of 21.10 µM.
Figure 25:
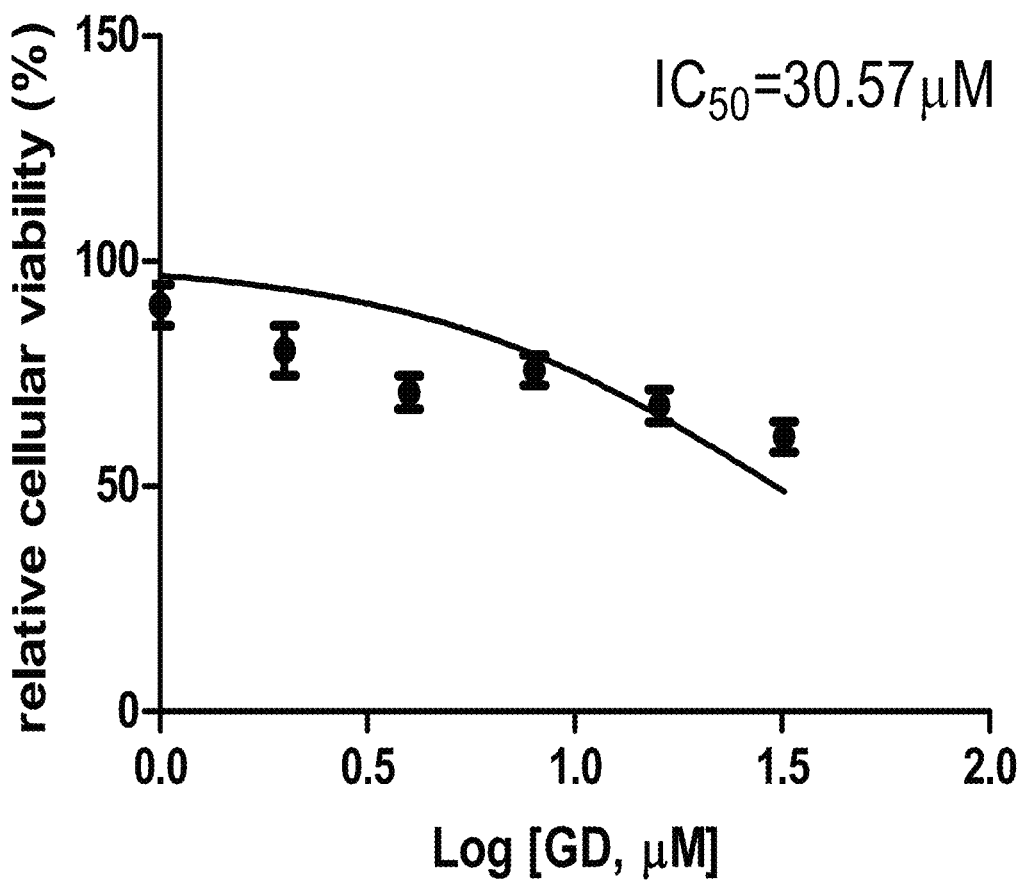
FIG. 25 is a graph of the relative cellular viability (%) of PMA-activated THP-1 macrophages as a function of the Log concentration (µm) of Doxorubicin loaded graphene quantum dots (GD), indicating relative low immunotoxicity induced by GD and an $IC_{50}$ of 30.57 µM.
Figure 26:
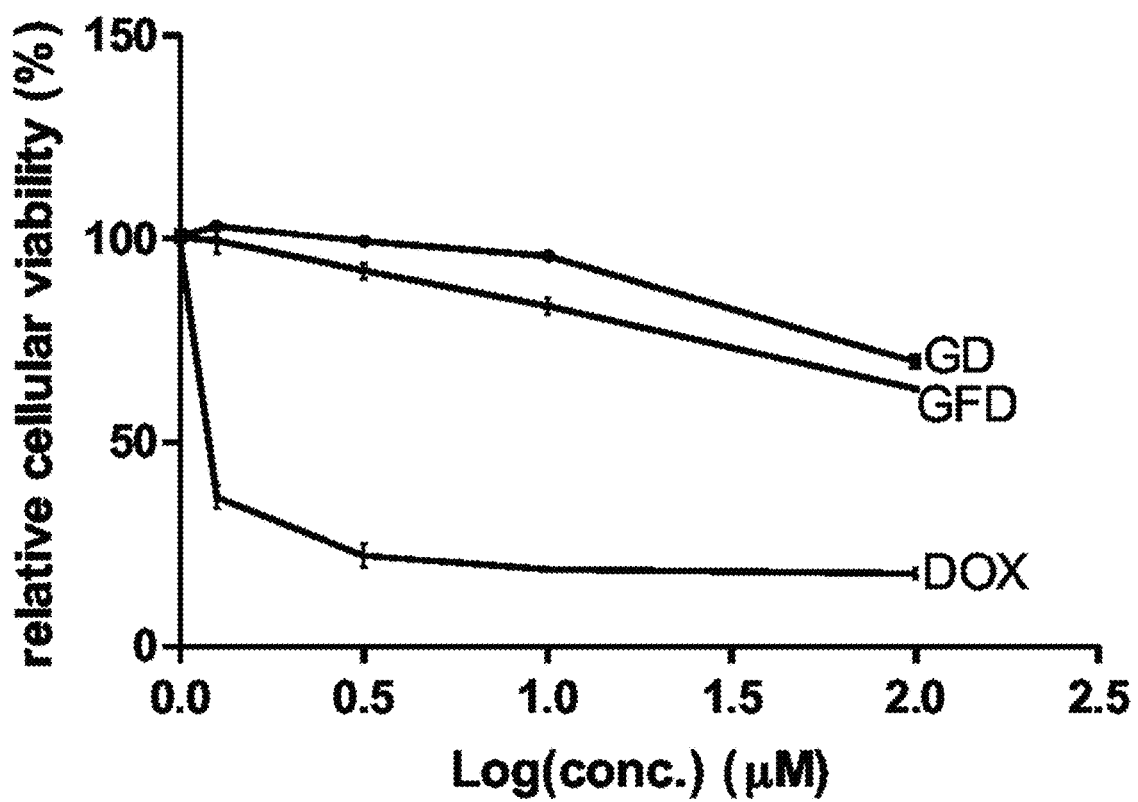
FIG. 26 is a graph of the relative cellular viability (%) of rat cardiac cell H9c2 as a function of the Log concentration (µm) of Doxorubicin (DOX), Doxorubicin loaded graphene quantum dots (GD), or Doxorubicin loaded graphene quantum dots with folic acid targeting ligands (GFD).
Figure 27:
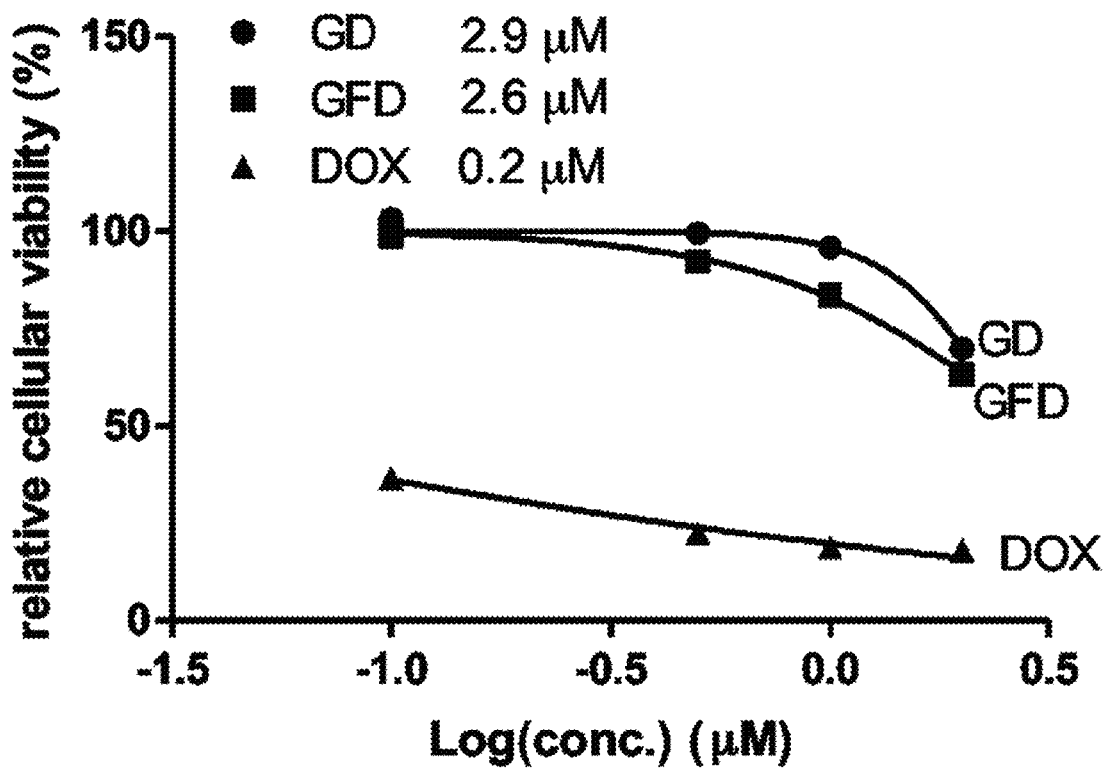
FIG. 27 is a graph of the relative cellular viability (%) of rat cardiac cell H9c2 as a function of Log concentration (µm) of Doxorubicin (DOX), Doxorubicin loaded graphene quantum dots (GD), or Doxorubicin loaded graphene quantum dots with folic acid targeting ligands (GFD), indicating relatively low toxicity to the cardiovascular system induced by GFD and GD as compared to DOX. The $IC_{50}$ values of GD, GFD, and DOX are given in the figure legend.

The adverse effect of Dox is known to cardiovascular system. To further examine the side effect of GQDs-FA-Dox on immune cells and cardiac cells compared to Dox, human macrophage cell line THP-1 and rat cardiac cell H9c2 were used. FIGS. 23 & 26 showed the relatively viability of PMA-activated THP-1 cells and H9c2 after treatment of GQDs-FA-Dox and GQDs-Dox, respectively. FIGS. 24 & 25 is the $IC_{50}$ of GQDs-FA-Dox and GQDs-Dox on PMA-activated THP-1 macrophages, respectively (i.e. 21.10 μM or 30.57 μM). FIGS. 26 & 27 shows the $IC_{50}$ of Dox, GQDs-FA-Dox, and GQDs-Dox on rat myoblast H9c2 respectively.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of making a plurality of conjugates, wherein each conjugate comprises a graphene quantum dot (GQD), a targeting moiety conjugated to the GQD, and an active agent associated with the GQD, wherein the GQDs in the plurality of conjugates have an average diameter of about 3 nm and a span of about 1.5 or less, wherein the targeting moiety is folic acid or a derivative thereof, and wherein the active agent is a doxorubicin noncovalentiv associated with the GQD via π-π stacking:
   the method comprising
   conjugating the targeting moiety to each GQD in the plurality of conjugates to form a plurality of first intermediates, wherein the targeting moiety is folic acid or a derivative thereof, and wherein the GQDs in the plurality of conjugates have an average diameter of about 3 nm and a span of about 1.5 or less;
   wherein conjugating the targeting moiety to each GQD comprises the steps of:
   reacting each GQD with ammonium hydroxide and hydrogen peroxide to introduce amine reactive coupling groups onto each of the GQDs; and
   reacting the targeting moiety with crosslinking agents to form a covalent bond with the amine reactive coupling group to form the plurality of first intermediates; and
   associating the active agent to each first intermediate in the plurality of first intermediates to form the plurality of conjugates, wherein the active agent is a doxorubicin noncovalently associated with the GQD via π-π stacking.

2. The method of claim 1, further comprising producing the GQDs by a method comprising the steps of
   combining a graphite with an oxidizing mixture comprising potassium permanganate ($KMnO_4$), sulfuric acid ($H_2SO_4$), and nitric acid ($HNO_3$) to form a combination; and
   heating the combination to an elevated temperature of about 120° C. to 180° C. with respect to room temperature to produce the GQDs.

3. The method of claim 2, wherein each GQD comprises faces and edges, and
   wherein the targeting moiety is conjugated to the edges.

4. The method of claim 1, wherein the crosslinking agents comprise N-hydroxysuccinimide (NHS) and 1-Ethyl-3-(3-dimethylaminopropyl)-carbodiimide (EDC).

5. The method of claim 1, wherein the GQDs have a monodisperse size distribution having a span of 1 or less, a coefficient of variation of 0.5 or less, or both.

6. The method of claim 1, wherein at least 40% of the GQDs have a diameter within ±0.5 nm of the average diameter of the GQDs.

* * * * *